United States Patent
McCarthy et al.

(10) Patent No.: US 8,404,485 B2
(45) Date of Patent: Mar. 26, 2013

(54) SYNTHETIC MICROCARRIERS FOR CULTURING CELLS

(75) Inventors: Kevin Robert McCarthy, Horseheads, NY (US); Simon Kelly Shannon, Horseheads, NY (US); Florence Verrier, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/557,771

(22) Filed: Jul. 25, 2012

(65) Prior Publication Data

US 2012/0288912 A1 Nov. 15, 2012

Related U.S. Application Data

(62) Division of application No. 12/844,255, filed on Jul. 27, 2010, now Pat. No. 8,257,828.

(60) Provisional application No. 61/229,114, filed on Jul. 28, 2009, provisional application No. 61/308,123, filed on Feb. 25, 2010.

(51) Int. Cl.
- *B32B 5/16* (2006.01)
- *B32B 9/00* (2006.01)
- *B32B 15/02* (2006.01)
- *B32B 17/02* (2006.01)
- *B32B 19/00* (2006.01)
- *B32B 21/02* (2006.01)

(52) U.S. Cl. ........ 435/402; 435/325; 435/395; 435/363; 435/366; 435/383; 435/397; 435/403

(58) Field of Classification Search .................... 435/402
See application file for complete search history.

(56) References Cited

U.S. PATENT DOCUMENTS

| 4,278,804 A | 7/1981 | Ashby et al. |
| 4,495,360 A | 1/1985 | Anthony |
| 5,173,421 A | 12/1992 | Kiniwa et al. |
| 2009/0136912 A1 | 5/2009 | Kurokawa et al. |
| 2009/0191627 A1 | 7/2009 | Fadeev et al. |
| 2009/0191632 A1 | 7/2009 | Fadeev et al. |

FOREIGN PATENT DOCUMENTS

| WO | 8905150 | 6/1989 |
| WO | 2009/099555 | 8/2009 |

OTHER PUBLICATIONS

Koide et al, 1993, Chem. Pharm. Bull. 41(3):502-6.
Koide et al, 1993, Chem. Pharm. Bull. 41(9);1596-1600.
Besse and Moroder, 1997, Journal of Peptide Science, vol. 3, 442-453.
Thompson (1998) Science 282:1145.
Genbacev et al., Fertil. Steril. 83(5):1517-29, 2005.
Cowan et al., NEJM 350(13):1353-56, 2004.
Klimanskaya et al., Lancet, 365(9471):1636-41, 2005.
Takahashi et al., (2007) Cell 131(5):861.
Yu et al., (2207) Science 318:5858.

*Primary Examiner* — Celine Qian
*Assistant Examiner* — Addison D Ault
(74) *Attorney, Agent, or Firm* — Susan S. Wilks

(57) ABSTRACT

A coated microcarrier for cell culture includes a microcarrier base and a polymeric coating grafted to the base via a polymerization initiator. A method for forming the coated microcarrier includes (i) conjugating a polymerization initiator to the microcarrier base to form an initiator-conjugated microcarrier base; (ii) contacting the initiator-conjugated microcarrier base with monomers; and (iii) activating the initiator to initiate polymerization and graft the polymer to the base.

14 Claims, 10 Drawing Sheets

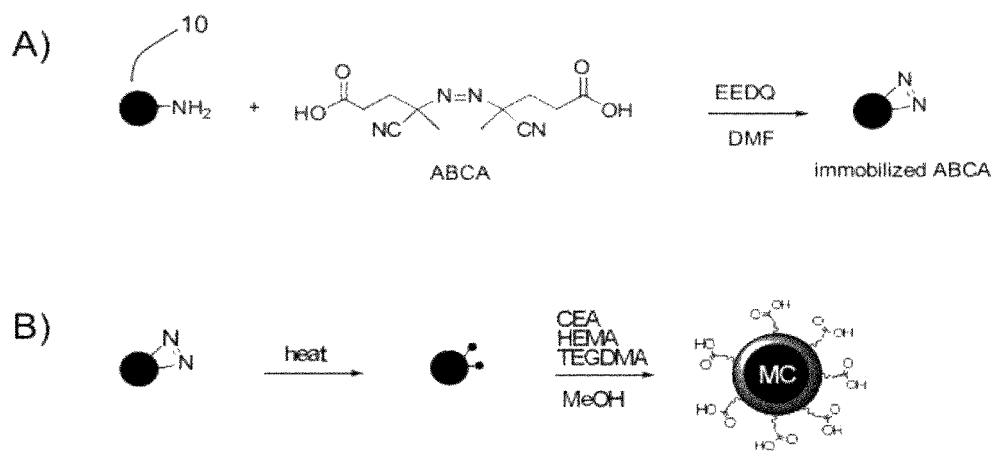
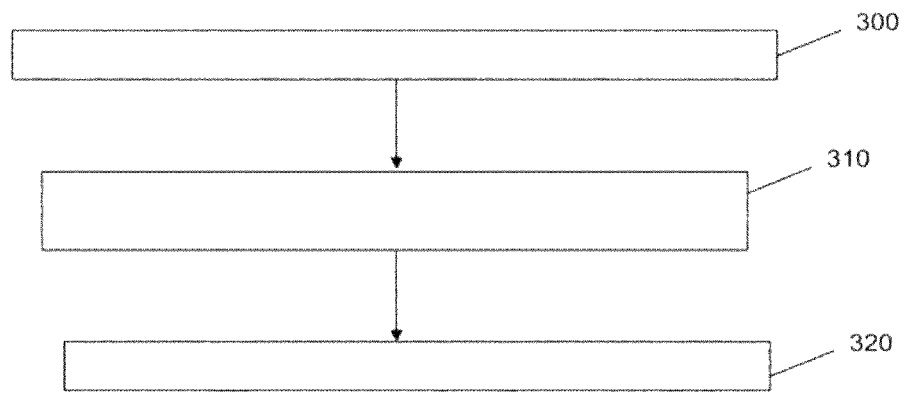
FIG. 5
FIG. 6

PS-ABCA-HG02-VN
A

PS-ABCA-HG02-VNScr
B

A

B

SYNTHETIC MICROCARRIERS FOR CULTURING CELLS

CLAMING BENEFIT OF PRIOR FILED U.S. APPLICATION

This application is a divisional of U.S. patent application Ser. No. 12/844,255 filed on Jul. 27, 2010 now U.S. Pat. No. 8,257,828, the content of which is relied upon and incorporated herein by reference in its entirety, and the benefit of priority under 35 U.S.C. §120 is hereby claimed.

This application claims the benefit of U.S. Provisional Application Ser. No. 61/229,114, filed on Jul. 28, 2009, and U.S. Provisional Application Ser. No. 61/308,123, filed Feb. 25, 2010. The content of this document and the entire disclosure of publications, patents, and patent documents mentioned herein are incorporated by reference.

FIELD

The present disclosure relates to cell culture microcarriers, and more particularly to synthetic, chemically-defined microcarriers.

SEQUENCE LISTING

This application contains a Sequence Listing electronically submitted via EFS-Web to the United States Patent and Trademark Office as text filed named "SP10046_ST25.txt" having a size of 8 kb and created on Jul. 21, 2010. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Microcarriers have been employed in cell culture for the purpose of providing high yields of attachment-dependent cells. Microcarriers are typically stirred or agitated in cell culture media and provide a very large attachment and growth surface area to volume ratio relative to more traditional culture equipment.

Most currently available microcarriers provide for non-specific attachment of cells to the carriers for cell growth. While useful, such microcarriers do not allow for biospecific cell adhesion and thus do not readily allow for tailoring of characteristics of the cultured cells. For example, due to non-specific interactions it may be difficult to maintain cells, such as stem cells, in a particular state of differentiation or to direct cells to differentiate in a particular manner.

Some currently available microcarriers provide for biospecific adhesion, but employ animal derived coating such as collagen or gelatin. Such animal derived coatings can expose the cells to potentially harmful viruses or other infectious agents which could be transferred to patients if the cells are used for a therapeutic purpose. In addition, such viruses or other infectious agents may compromise general culture and maintenance of the cultured cells. Further, such biological products tend to be vulnerable to batch variation and limited shelf-life.

Some synthetic, chemically-defined surfaces have been shown to be effective in culturing cells, such as embryonic stem cells, in chemically defined media. However, the ability of such surfaces to support 3D culture on microcarriers has not yet been reported and methods for applying such surfaces to microcarriers have not yet been described.

BRIEF SUMMARY

Among other things, the present disclosure describes synthetic, chemically-defined microcarriers useful in culturing cells. The microcarriers, in various embodiments, are coated with a cross-linked swellable (meth)acrylate surface. The present disclosure also describes processes for grafting coatings, such as the cross-linked swellable methacrylate surfaces, to microcarriers.

In various embodiments, a microcarrier includes a microcarrier base and a cross-linked polymeric coating grafted to the base via a polymerization initiator. The microcarrier may further include a polypeptide conjugated to the coating. The microcarriers may be formed by (i) conjugating a polymerization initiator to the microcarrier base to form an initiator-conjugated microcarrier base; (ii) contacting the initiator-conjugated microcarrier base with monomers; and (iii) activating the initiator to initiate polymerization and graft the polymer to the base.

Preferably, transfer of radicals into the solution phase is limited following activation of the initiator. Because the polymeric surfaces are cross-linked (i.e., formed from at least one di- or higher-functional monomer), it is desirable to limit polymerization to the surface of the microcarrier or polymer forming on the microcarrier to avoid clump-like formation of globs of microcarriers rather than desired individually coated microcarriers. Furthermore, cross-linked polymer in the bulk solution that is not grafted to the base bead would be challenging to separate from the individually coated beads due to insolubility.

One or more of the various embodiments presented herein provide one or more advantages over prior articles and systems for culturing cells. For example, synthetic microcarriers described herein have been shown to support cell adhesion without the need of animal derived biocoating which limits the risk of pathogen contamination. This is especially relevant when cells are dedicated to cell therapies. Further, large scale culture of cells, including human embryonic stem cells (hESCs), is possible with microcarriers as described herein. Such microcarriers may also be advantageously used for culturing cells other than stem cells when animal derived products such as collagen, gelatin, fibronectin, etc. are undesired or prohibited. The methods described herein allow for the preparation of microcarriers having a wide range of properties such as stiffness, swellability, density, and surface chemistries. These and other advantages will be readily understood from the following detailed descriptions when read in conjunction with the accompanying drawings

BRIEF DESCRIPTION OF THE DRAWINGS

FIGS. 5A-B are collectively a reaction scheme of an embodiment of a method for forming a coated microsphere.

FIG. 6 is a flow diagram of an embodiment of a method of forming a coated microsphere.

Figure 1:
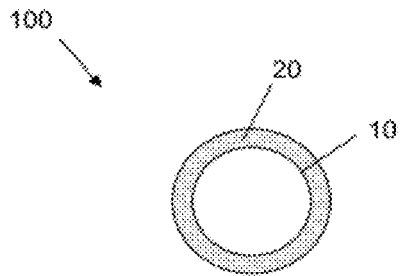
FIG. 1 is a schematic drawing of a cross-section of an embodiment of a coated microcarrier.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Polypeptide sequences are referred to herein by their one letter amino acid codes and by their three letter amino acid codes. These codes may be used interchangeably.

As used herein, "monomer" means a compound capable of polymerizing with another monomer, (regardless of whether the "monomer" is of the same or different compound than the other monomer), which compound has a molecular weight of less that about 1000 Dalton. In many cases, monomers will have a molecular weight of less than about 400 Dalton.

As used herein, "microcarrier" means a small discrete particle for use in culturing cells and to which cells may attach. Microcarriers may be in any suitable shape, such as rods, spheres, and the like. In many embodiments, a microcarrier includes a microcarrier base that is coated to provide a surface suitable for cell culture. A polypeptide may be bonded, grafted or otherwise attached to the surface coating.

As used herein "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD.

Polypeptides may be of any suitable length, such as between three and 30 amino acids in length. Polypeptides may be acetylated (e.g. Ac-LysGlyGly) or amidated (e.g. SerLysSer-NH$_2$) to protect them from being broken down by, for example, exopeptidases. It will be understood that these modifications are contemplated when a sequence is disclosed.

As used herein, "equilibrium water content" refers to water-absorbing characteristic of a polymeric material and is defined and measured by equilibrium water content (EWC) as shown by Formula 1:

$$EWC\ (\%) = [(W\text{gel} - W\text{dry})/(W\text{gel})] * 100. \qquad \text{Formula 1}$$

As used herein, a "remnant" of a polymerization initiator means a portion of the initiator that results from activation of the initiator to produce free radicals. For example, a polymerization initiator may form a free radical-containing remnant following thermal, photolytic or catalytic activation, which result in inter- or intra-molecular bond dissociation, hydrogen abstraction or other known initiator mechanisms. A photo initiator may have two ends which each attach to a microcarrier. When the system is exposed to an energy source, the initiator may break apart, creating a free radical. In this case, only a remnant of the initiator is present to initiate polymerization.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. Accordingly, a microcarrier comprising a microcarrier base and a coating includes a microcarrier consisting essentially of, or consisting of, a microcarrier base and a coating.

The present disclosure describes, inter alia, synthetic microcarriers for culturing cells. In various embodiments, the microcarriers are configured to support proliferation and maintenance of undifferentiated stem cells in chemically defined media.

1. Microcarrier

Figure 2:
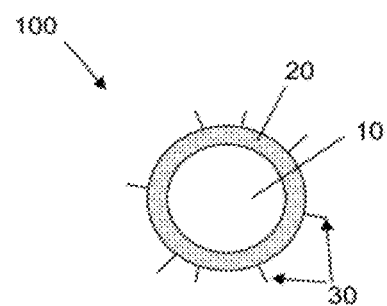
FIG. 2 is a schematic drawing of a cross-section of an embodiment of a coated microcarrier with a conjugated polypeptide.

Referring to FIG. 1 and FIG. 2, a microcarrier 100 includes a base 10 and a coating 20 and may include a conjugated polypeptide 30. The coating 20 alone or coating 20 and polypeptide 30 together provide a surface to which cells can attach for the purposes of cell culture. In various embodiments, the coating layer 20 is deposited on or formed on a surface of an intermediate layer that is associated with the base material 10 via covalent or noncovalent interactions, either directly or via one or more additional intermediate layers (not shown). In such cases, the intermediate is considered, for the purposes of this disclosure, to be a part of the microcarrier base 10.

Microcarriers can have any suitable density. However, it is preferred that microcarriers have a density slightly greater than the cell culture medium in which they are to be suspended to facilitate separation of the microcarriers from the surrounding medium. In various embodiments, the microcarriers have a density of about 1.01 to 1.10 grams per cubic centimeter. Microcarriers having such a density should be readily maintained in suspension in cell culture medium with gentle stirring.

It is also preferred that the size variation of the microcarriers is small to ensure that most, if not all, of the microcarriers can be suspended with gentle stirring. By way of example, the geometric size distribution of the microcarriers may be between about 1 and 1.4. Microcarriers may be of any suitable size. For example, microcarriers may have a diametric dimension of between about 20 microns and 1000 microns. Spherical microcarriers having such diameters can support the attachment of several hundred to thousands of cells per microcarrier. The size of the microcarrier bases, and thus the overall microcarrier, can be readily controlled. By way of example, microcarrier bases formed via water-in-oil copolymerization techniques can be easily tuned by varying the stirring speed or the type of emulsifier used. For example, higher stirring speeds tend to result in smaller particle size. In addition, it is believed that the use of polymeric emulsifiers, such as ethylcellulose, enables larger particles relative to lower molecular weight emulsifiers. Accordingly, one can readily modify stirring speed or agitation intensity and emulsifier to obtain microcarrier bases of a desired particle size.

Microcarriers can be porous or non-porous. As used herein, "non-porous" means having no pores or pores of an average size smaller than a cell with which the microcarrier is cultured, e.g., less than about 0.5-1 micrometers. Non-porous microspheres are desired when the microcarriers are not degradable, because cells that enter pores of macroporous microcarriers are difficult to remove. However, if the microcarriers are degradable, e.g. if they include an enzymatically or otherwise degradable cross-linker, it may be desirable for the microcarriers to be macroporous.

2. Microcarrier Base

Any suitable microcarrier base may be used. In various embodiments the microcarrier base is formed from glass, ceramic, metal or polymeric material. Examples of polymeric materials that can be used to create microcarriers include polystyrenes, acrylates such as polymethylmethacryate, acrylamides, agarose, dextrans, gelatins, latexes, and the like. The microcarrier base may have special characteristics such as being magnetic to ease separation from bulk media. In some embodiments, the microcarriers are microspheres, many of which are commercially available. Microspheres can be produced by any suitable method and are typically produced by suspension polymerization of a "water-in-oil"-type emulsion.

3. Coating

A microcarrier base may be coated with polymer from any suitable class of biocompatible polymers such as poly(meth) acrylates, polyamides, polyphosphazenes, polypropylfumarates, synthetic poly(amino acids), polyethers, polyacetals, polycyanoacrylates, poly(meth)acrylamides, polyurethanes, polycarbonates, polyanhydrides, poly(ortho esters), polyhydroxyacids, polyesters, ethylene-vinyl acetate polymers, cellulose acetates, polystyrenes, poly(vinyl chloride), poly(vinyl fluoride), poly(vinyl imidazole), poly(vinyl alcohol), chlorosulphonated polyolefins, and combinations thereof.

"Coating", "layer", "surface", "material", and the like are used interchangeably herein, in the context of a polymer disposed on a microcarrier base. Preferably, the coating is a synthetic polymer coating free from animal-derived components, as animal derived components occasionally may contain viruses or other infectious agents or may provide a high level of batch-to-batch variability. In various embodiments, the coating is a hydrogel coating or a swellable (meth)acrylate coating, e.g., as described in U.S. patent application Ser. No. 12/362,924, filed on Jan. 30, 2009, entitled SYNTHETIC SURFACES FOR CULTURING CELLS IN CHEMICALLY DEFINED MEDIA, and published on Jul. 30, 2009 as US 2009/0191627; and U.S. patent application Ser. No. 12/362,974, filed on Jan. 30, 2009, entitled SWELLABLE (METH) ACRYLATE SURFACES FOR CULTURING CELLS IN CHEMICALLY DEFINED MEDIA, and published on Jul. 30, 2009 as US 2009/0191632, which applications are hereby incorporated herein by reference in their respective entireties to the extent that they do not conflict with the disclosure presented herein.

As used herein, "swellable (meth)acrylate" or "SA" means a polymer matrix made from at least one ethylenically unsaturated monomer (acrylate or methacrylate monomers) having at least some degree of cross linking, and also having water absorbing or water swelling characteristics. "SAP", as used herein, means as SA conjugated to a polypeptide or protein. In embodiments, the term "swellable (meth)acrylate" represents a range of cross-linked acrylate or methacrylate materials which absorb water, swell in water, and do not dissolve in water.

In various embodiments, the SA coating comprises, consists essentially of, or consists of, reaction products of one or more hydrophilic (meth)acrylate monomer, one or more di- or higher-functional (meth)acrylate monomer ("cross-linking" (meth)acrylate monomer), and one or more carboxyl group-containing monomers. Any suitable hydrophilic (meth)acrylate monomer may be employed. Examples of suitable hydrophilic (meth)acrylate monomers include 2-hydroxyethyl methacrylate, di(ethylene glycol)ethyl ether methacrylate, ethylene glycol methyl ether methacrylate, and the like. In various embodiments, hydrophilic monomers other than (meth)acrylates may be used to form the SA coating. These other hydrophilic monomers may be included in addition to, or in place of, hydrophilic (meth)acrylate monomers. Such other hydrophilic monomers should be capable of undergoing polymerizing with (meth)acrylate monomers in the mixture used to form the swellable (meth)acrylate layer. Examples of other hydrophilic monomers that may be employed to form the SA coating include 1-vinyl-2-pyrrolidone, acrylamide, 3-sulfopropyldimethyl-3-methylacrylamideopropyl-ammonium, and the like. Regardless of whether a (meth)acrylate monomer or other monomer is employed, a hydrophilic monomer, in various embodiments, has a solubility in water of 1 gram or more of monomer in 100 grams of water. Any suitable di- or higher-functional (meth)acrylate monomer, such as tetra(ethylene glycol)dimethacrylate or tetra(ethylene glycol)diacrylate, may be employed as a cross-linking monomer. Any suitable (meth)acrylate monomer having a carboxyl functional group available for conjugating with a polypeptide after the monomer is incorporated into the SA coating by polymerization may be employed. The carboxyl functional group enables conjugation of a peptide or polypeptide using NHS/EDC chemistry. Examples of suitable carboxyl group-containing (meth)acrylate include 2-carboxyethyl acrylate, acrylic acid and mono-(2-methacryoyloxyl)-ethyl succinate.

In various embodiments, the SA layer is formed from monomers comprising (by percent volume): hydrophilic (meth)acrylate monomer (~60-90), carboxyl group-containing (meth)acrylate monomer (~10-40), and cross-linking (meth)acrylate monomer (~1-10), respectively. It will be understood that the equilibrium water content (EWC) of the SA layer may be controlled by the monomers chosen to form the SA layer. For example, a higher degree of hydrophilicity and a higher percentage of the hydrophilic monomer should result in a more swellable SA layer with a higher EWC. However, this may be attenuated by increasing the percentage, or increasing the functionality, of the cross-linking monomer, which should reduce the ability of the SA layer to swell and reduce the EWC.

In various embodiments, the specific monomers employed to form the SA layer and their respective weight or volume percentages are selected such that the resulting SA layer has an EWC of between about 5% and about 70%. Due in part to the use of a carboxyl containing monomer in the SAs of various embodiments described herein, the EWC may be pH dependent. For example, the EWC of particular SAs may be higher in phosphate buffer (pH 7.4) than in distilled, deionized water (pH ~5). In various embodiments, the EWC of an SA layer in distilled, deionized water is the EWC (in water) of SAs of the present invention may range between 5% and 70%, between 5% and 60%, between 5% and 50%, between 5 and 40%, between 5% and 35%, between 10% and 70%, between 10% and 50% between 10 and 40%, between 5% and 35%, between 10% and 35% or between 15% and 35% in water. In further embodiments, after the swellable (meth)acrylates have been conjugated with peptides (SAP), the EWC of embodiments of SAPs may be, for example, between 10-40% in water.

In cell culture, prepared surfaces are exposed to an aqueous environment for extended periods of time. Surfaces that absorb significant water, surfaces that are highly hydrogel-like, may tend to delaminate from a substrate when exposed to an aqueous environment. This may be especially true when these materials are exposed to an aqueous environment for extended periods of time, such as for 5 or more days of cell culture. Accordingly, it may be desirable for SA and SAP layers to have lower EWC measurements, so that they do not absorb as much water, to reduce the likelihood of delaminating. For example, SA surfaces having an EWC below 40% may be particularly suitable for supporting cells in culture, including human embryonic stem cells.

It will be understood that the conjugation of a polypeptide to an SA layer may affect the swellability and equilibrium water content (EWC) of the SA layer, generally increasing the EWC. The amount of polypeptide conjugated to SA layers tends to be variable and can change depending on the thickness of the SA layer. Accordingly, the EWC of a SA-polypeptide layers prepared in accordance with a standard protocol may be variable. For purposes of reproducibility, it may be desirable to measure the EWC of SA layers prior to conjugation with a polypeptide. With this noted, in some embodiments, after the SAs have been conjugated with polypeptides (SA-polypeptide), the EWC of embodiments of SA-polypeptide layers may be between about 10% and about 40% in water.

In various embodiments, the SA layer includes polymerized (meth)acrylate monomers formed from a mixture including hydroxyethyl methacrylate, 2-carboxyethylacrylate, and tetra(ethylene glycol)dimethacrylate. In numerous embodiments, the ratio (by volume) of hydroxyethyl methacrylate, 2-carboxyethylacrylate, and tetra(ethylene glycol) dimethacrylate used to form the SA layer is about 80/20/3 (v/v/v), respectively. In some embodiments, the SA is formulated using the following liquid aliquots of monomers (by volume): hydroxyethyl methacrylate (~60-90), 2-carboxyethylacrylate (~10-40), and tetra(ethylene glycol) dimethacrylate (~1-10), respectively. In numerous embodiments, the SA layer consists essentially of polymerized hydroxyethyl methacrylate, 2-carboxyethylacrylate, and tetra(ethylene glycol)dimethacrylate monomers. In various embodiments, the SA layer is substantially free of polypeptide crosslinkers.

Some representative swellable (meth)acrylate formulations that may be employed are illustrated in Table 1

TABLE 1

| Swellable (meth)acrylate formulations | | | |
|---|---|---|---|
| Formualtion No. | Hydrophilic Monomer (vol. %) | Carboxyl group containing monomer (vol. %) | Crosslinking monomer (vol. %) |
| 1 | hydroxyethyl methacrylate (80) | 2-carboxyethyl acrylate (20) | Tetra(ethylene glycol) dimethacrylate (3) |
| 2 | hydroxyethyl methacrylate (60) | 2-carboxyethyl acrylate (40) | Tetra(ethylene glycol) dimethacrylate (3) |
| 3 | poly(ethylene glycol)(600) dimethacrylate (80) | 2-carboxyethyl acrylate (20) | |
| 4 | hydroxyethyl methacrylate (90) | 2-carboxyethyl acrylate (10) | Tetra(ethylene glycol) dimethacrylate (3) |

TABLE 1-continued

Swellable (meth)acrylate formulations

| Formualtion No. | Hydrophilic Monomer (vol. %) | Carboxyl group containing monomer (vol. %) | Crosslinking monomer (vol. %) |
|---|---|---|---|
| 5 | hydroxyethyl methacrylate (70) | 2-carboxyethyl acrylate (30) | Tetra(ethylene glycol) dimethacrylate (3) |
| 6 | Hydroxypropyl methacrylate(80) | 2-carboxyethyl acrylate (20) | Tetra(ethylene glycol) dimethacrylate (3) |
| 7 | 2-Hydroxyethyl acrylate(80) | 2-carboxyethyl acrylate (20) | Tetra(ethylene glycol) dimethacrylate (3) |
| 8 | 1-vinyl-2-pyrrolidone(80) | 2-carboxyethyl acrylate (20) | Tetra(ethylene glycol) dimethacrylate (3) |
| 9 | Di(ethylene glycol) ethyl ether methacrylate(80) | 2-carboxyethyl acrylate (20) | Tetra(ethylene glycol) dimethacrylate (3) |
| 10 | Acrylamide(80) | 2-carboxyethyl acrylate (20) | Tetra(ethylene glycol) dimethacrylate (3) |
| 11 | Ethylene glycol methyl ether methacrylate(80) | 2-carboxyethyl acrylate (20) | Tetra(ethylene glycol) dimethacrylate (3) |
| 12 | 3-sulfopropyldimethyl-3-methacrylamidopropyl-ammonium(80) | 2-carboxyethyl acrylate (20) | Tetra(ethylene glycol) dimethacrylate (3) |

A polymer coating layer may have any desirable thickness. In various embodiments, the average thickness of the coating layer is less than about 100 micrometers. For example, the average thickness may be less than about 50 micrometers, less than about 20 micrometers, less than about 10 micrometers, less than about 5 micrometers, less than about 2 micrometers, less than about 1 micrometer, less than about 0.5 micrometers, between about 50 nm and about 300 nm, or about 0.1 micrometers. It will be understood that the coating thickness will depend on several variables, including the grafting technique employed, the reaction conditions, the reaction time, and the technique used to measure the coating thickness. For example, coating thickness measured by SEM in the dry state may be different if from the same measured in its hydrated state using a technique such as confocal microscopy in buffered solutions.

4. Coating of Microcarrier Base with Polymer

A polymer layer may be disposed on a surface of a microcarrier base via any known or future developed process. In embodiments, the coating provides a uniform layer that does not delaminate during typical cell culture conditions. The coating layer may be associated with the microcarrier base via covalent or non-covalent interactions. Examples of non-covalent interactions that may associate the synthetic SA surface with the substrate include chemical adsorption, hydrogen bonding, surface interpenetration, ionic bonding, van der Waals forces, hydrophobic interactions, dipole-dipole interactions, mechanical interlocking, and combinations thereof. Examples of covalent interactions include copolymerization of the (meth)acrylate monomers with a microcarrier base containing either a polymerizable group (e.g., acrylate), a group capable of fragmenting to produce free radical, or chain transfer agent, and combinations thereof.

In numerous embodiments, monomers are brought in contact with the surface of a microcarrier base and polymerized in situ. In such embodiments, the base will be referred to herein as the "substrate" on which the polymer is deposited or formed. Polymerization may be done in solution phase or in bulk phase. The substrate is suspended in the monomer mixture and polymerization is initiated at the surface of the substrate. As monomers may be viscous, it may be desirable to dilute the monomers in a suitable solvent to reduce viscosity prior to suspending the microcarrier base substrate. Reducing viscosity may allow for thinner and more uniform layers of the coating material to be formed. Preferably the solvent is compatible with the microcarrier base material and the monomers. It may be desirable to select a solvent that is nontoxic to the cells to be cultured and that does not interfere with the polymerization reaction. Alternatively, or in addition, selection of a solvent that can be substantially completely removed or removed to an extent that it is non-toxic or no longer interferes with polymerization may be desirable. In such circumstances, it may be desirable that the solvent be readily removable without harsh conditions, such as vacuum or extreme heat. Volatile solvents are examples of such readily removable solvents.

Some solvents that may be suitable in various situations for coating articles as described herein include methanol, ethanol, acetone, butanone, acetonitrile, 2-butanol, isopropanol, acetyl acetate, ethyl acetate, dimethylformamide (DMF), dimethylsulfoxide (DMSO), water or combinations thereof.

The monomers may be diluted with solvent by any suitable amount to achieve the desired viscosity and monomer concentration. For example, the monomer compositions may contain between about 0.1% to about 99% monomer. By way of example, the monomer may be diluted with an ethanol or other solvent to provide a composition having between about 0.1% and about 50% monomer, or from about 0.1% to about 10% monomer by volume, or from about 0.1% to about 1% monomer by volume. The monomers may be diluted with solvent so that the coating layer achieves a desired thickness. The layer thickness may also be controlled by polymerization reaction time, monomer to initiator concentration ratio, or the like.

In addition to the monomers that form the coating layer, a composition forming the layer may include one or more additional compounds such as surfactants, wetting agents, polymerization initiators, catalysts or activators.

Whether polymerized in bulk phase (substantially solvent free) or solvent phase, the monomers are polymerized via an appropriate initiation mechanism. Many of such mechanisms are known in the art. For example, temperature may be increased to activate a thermal initiator, photoinitiators may be activated by exposure to appropriate wavelength of light, redox systems may be activated by oxidation reduction chemical initiator pairing, or the like. Polymerization may be carried out under inert gas protection, such as nitrogen protection, to prevent oxygen inhibition.

Any suitable polymerization initiator that can be immobilized may be employed. One of skill in the art will readily be able to select a suitable initiator, e.g. a radical initiator or a cationic initiator, suitable for use with the monomers. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, diethyl dithiocarbamates, bromo or hydroxy acids or acid halides, or mixtures thereof. Preferably, the initiator is capable of providing surface initiated grafting of the forming polymer (i.e., grafting from the surface) and minimizes grafting in solution. Grafting from the surface is desirable when the forming polymer is cross-linked (i.e., formed from one or more di- or higher functional monomer). Non-limiting examples of monomers capable of grafting from the surface with minimal or no transfer of radicals away from the surface include 4,4'-Azobis-(4-cyanopentanoic acid) (ACBA), 4-(3-hydridodiethylsilyl)propyloxybenzophone, (3-(2-bromoisobutyryl)propyl)diethylhydridosilane, and 2-bromo-isobutyryl bromide. For some initiators, such as ACBA, which splits to form two radicals, the initiator is preferably anchored to the surface via two anchoring groups such that each radical containing moiety remains bound to the surface and does not migrate away from the surface.

The initiator may be conjugated or immobilized (i.e., covalently bound) to the microcarrier base via any suitable method. To facilitate the conjugation of an initiator to the surface of a microcarrier base, the microcarrier base may include a functional group suitable for reaction with the initiator. The microcarrier base may include any suitable functional group, and the suitability of the functional group may depend on the initiator used. For example, if either one of the functional group of the microcarrier base or the polymerization initiator has an available carboxylic acid group, the hydroxyl group of the carboxylic acid may be replaced by a suitable nucleophile, such as a nitrogen of an amine (via an amidation reaction) or an oxygen of an alcohol (via an esterification reaction). By way of further example, the microcarrier may be glass (or contain an available silanol group) and the polymerization initiator may have an available silane coupling group (or hydrolysable group such as alkoxy, acyloxy, or halogen). Not to be bound by theory, it is believed that the hydrolysable group of the polymerization initiator first hydrolyzes, condenses (loss of water) into silanol-oligomer and then hydrogen bonds to the OH groups of the glass. Heat is then introduced to promote condensation resulting in a covalent linkage formed with the initiator and the glass microcarrier. These aforementioned reactions may all occur simultaneously after the initial hydrolysis of the hydrolysable groups.

Factors such as initial concentration of surface hydroxyls, type of surface hydroxyls, stability of the bond formed and dimensions/features of the substrate may influence the effectiveness of the initiator coupling. It is often desirable to have the maximum number of accessible reactive sites on the glass microcarrier to maximize initiator coupling. Acid or base etching (e.g., 1M sodium hydroxide, ammonia, hydrochloric acid), UV-ozone, or plasma treatment may be included as a step to pretreat the glass microcarrier to clean and/or expose more reactive silanol groups which may interact with the silane-initiator. Other hydroxyl-containing substrates such as silica, quartz, aluminum, alumino-silicates, copper inorganic oxides, etc. may be used as an alternative to glass.

In some embodiments, the initiator is selected and immobilized in a way so that polymerization takes place at the surface of the microcarrier base with minimal polymerization in solution, which may be desirable in situations where insoluble crosslinked polymers, which can become difficult to remove from the bulk polymerization mixture, are grafted. Surface initiators include reversible addition-fragmentation chain transfer (RAFT), atom transfer radical polymerization (ATRP), or other surface initiators. Suitable activators, as readily identifiable in the art, may be employed to facilitate such reactions.

Examples of suitable reactions may include, amide bond formation using EDC/NHS activation, HATU/DIEA, EEDQ and other amide bond forming reactions. Initiators containing isothiocyanate, isocyanate, acyl halde, aldehyde, epoxy, anhydride, or other amine reactive groups may be immobilized onto an amine containing microcarrier base support. Initiators containing, maleimides, thiols, and the like may be immobilized onto thiol microcarrier base supports by Michael addition or disulfide forming reactions. Initiators containing hydroxyl or amine groups can be immobilized onto epoxide or oxiraine microcarrier base supports by nucleophilic ring opening mechanisms. Cycloaddition reactions such as click chemistry, Diels-Alder reactions may be employed as immobilization methods. Affinity reactions such as biotin/Streptavidin, or protein A/immunoglobulin G interactions may be used for initiator immobilization. The support or the initiator may contain the appropriate function group to facilitate immobilization. For example, as described herein, a carboxylic acid containing initiator may be immobilized onto an amine containing microcarrier base support using EEDQ activation of the COOH-containing initiator. The reverse scenario, i.e., an amine containing initiator being immobilized to a COOH microcarrier base support, can also be envisioned. The other surface conjugation techniques described in the literature may also be applied for initiator immobilization. Such techniques have been thoroughly reviewed in the literature (Hermanson, G. T. Bioconjugate Techniques. Second Edition; Academic Press; Elsevier Inc. 2008).

By way of example, polymerization initiators having available carboxylic acid groups include 4,4'-azobis(4-cyanovaleric acid) (ABCA), and 4-benzoyl benzoic acid. Non-limiting examples of polymerization initiators having available hydroxyl groups include 2,2'-azobis[2-methyl-N-(2-hydroxyethyl)propionamide] and 2,2'-azobis{2-methyl-N-[1,1-bis(hydroxymethyl)-2-hydroxyethyl]propionamide} available from Wako Specialty chemicals under the trade name VA-086 or VA-080 respectively. Examples of photolyzable or ATRP initiators containing silane groups include 4-(3-hydridodiethylsilyl)propyloxybenzophone or (3-(2-bromoisobutyryl)propyl)diethylhydridosilane, respectively. An example of amine reactive ATRP initiator is 2-bromo-isobutyryl bromide available from Sigma. An example of a nucleophilic photo chain transfer initiator is diethyldithiocarbamate sodium salt available from GangFu Fine chemicals.

As mentioned above, a photoinitiator containing a silane coupling group may readily conjugated to glass (or other hydroxide-containing substrate; e.g. most inorganics). For example, such an initiator may be conjugated to a glass microcarrier or a microcarrier having available hydroxyl groups by contacting the initiator with the microcarrier, followed by a heat promoted condensation step; e.g. as discussed above.

Any suitable initiator may be formed into a silyl ether. In various embodiments the silyl ether initiator is of the following formula:

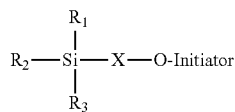

In various embodiments $R_1$, $R_2$, and $R_3$ are each independently substituted or unsubstituted C1-C3 alkyl, alkoxy, or hydrogen; and X is C1-C6 straight or branched chain substituted or unsubstituted alkyl and may be present or absent. By way of example, the silyl ether initiator is an alkoxy-substituted silyl benzophenone, such as those described in U.S. Pat. Nos. 4,495,360 and 4,278,804. One suitable alkoxy-substituted silyl benzophenone is 2-hydroxy-4(3-triethxysilylpropoxy)-dephenylketone (HDPK-Si).

In general, the amount of immobilized initiator will depend on the functional group loading of the microcarrier base support. Typically for crosslinked polystyrene, functionalities from 0.1 to 2 mmol/g of bead are available for various functional groups such as hydroxyl, amino and carboxylic acid. In some embodiments, the initiator is immobilized in a way so that polymerization takes place at the surface of the microcarrier base with minimal polymerization in solution, which may be desirable in situations where insoluble crosslinked polymers are grafted. In various embodiments, the immobilization level of the initiator is less than about 100% of the initial reactive functional group loading. For example, initiator level may be less than about 75% of the initial reactive functional group loading, less than about 50% of the initial reactive functional group loading, less than about 25% of the initial reactive functional group loading, less than about 10% of the initial reactive functional group loading, less than about 5% of the initial reactive functional group loading, or about 1% of the functional group loading. By way of example, the polymerization initiator, 4,4'-azobis(4-cyanovaleric acid) (ABCA), is immobilized so that all carboxylic acid groups are tied to the surface of the microcarrier base support. When the azo initiator fragments, both free radical groups remain tied to the surface with minimal radicals in the bulk solution. Similarly, the conjugation of the benzophenone from 2-hydroxy-4(3-triethxysilylpropoxy)-dephenylketone (HDPK-Si) to the surface of a glass microcarrier leaves the initiator bound to the surface by intermolecular hydrogen abstraction. By immobilizing both of the free radical groups to the base, bulk polymerization in solution can be limited.

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethylethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp. However, if a photosensitizer is used, it preferably minimizes polymerization in solution.

The cured coating layer may be washed with solvent one or more times to remove impurities such as unreacted monomers or low molecular weight polymer species. In various embodiments, the layer is washed with ethanol or an ethanol/water solution, e.g. 50% ethanol, 70% ethanol, greater than 90% ethanol, greater than 95% ethanol or greater than about 99% ethanol. The size and shape of the base microcarrier support allows facile and thorough washing of the coated microcarrier substrate. Any suitable filter apparatus may be incorporated to remove the washing solvent. Examples of filter systems are peptide synthesis vessels equipped with a vacuum filter or a soxhlet apparatus for higher temperature washings.

Figure 3:
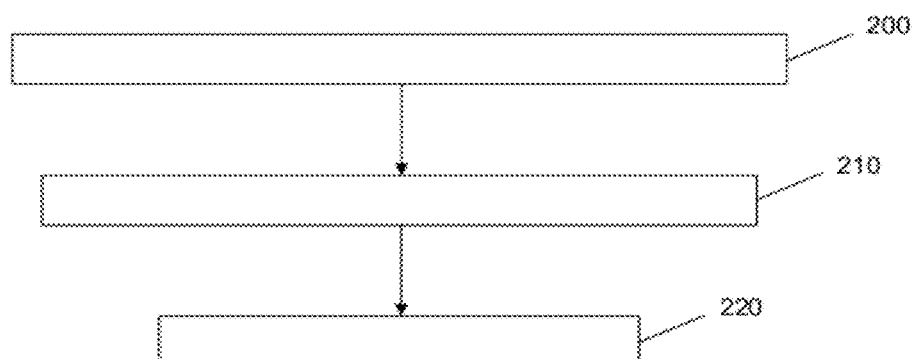
FIG. 3 is a flow diagram of an embodiment of a method of forming a coated microsphere.

Referring now to FIG. 3, the polymer layer may be grafted (e.g., covalently bound) to the microcarrier base as it is formed in situ while in contact with the microcarrier base. As shown in FIG. 3, in various embodiments, a method for grafting a coating layer to a microcarrier includes (i) conjugating covalently binding a polymerization initiator to the microcarrier base (200), and (ii) polymerizing and grafting the coating to the microcarrier base in situ while in contact with the base (210). The method may further include conjugating a polypeptide to the coating layer (210), e.g. as discussed in more detail below.

Many suitable functionalized microcarrier substrates are available from commercial sources. For example, COOH, SH, NH$_2$, and CHO functionalized polystyrene resins and microspheres are available from Rapp Polymere GMBH; amino, carboxylate, carboxy-sulfate, hydroxylate, and sulfate functionalized polystyrene beads are available from Polysciences, Inc.; and amine functionalized glass beads available from Polysciences, Inc. Carboxylate functionalized dextran beads are available from GE Healthcare, Hyclone, and Sigma-Aldrich. Azlactone functionalized beads are available from Pierce. Unfunctionalized magnetic beads are available from Merck.

Of course, functional groups may readily be added to microcarriers via techniques known in the art. For example, glass carriers may be readily functionalized with an appropriate organosilane. It may be desirable to treat or etch the surface of the glass carrier prior to functionalization to increase surface area. Functionalized epoxy resins may be employed to functionalize glass or other suitable microcarriers. Polystyrene or other suitable microcarriers can also be readily functionalized using known techniques. For example, a microcarrier base may be prepared by polymerization of monomers such as chloromethylstyrene or 4-t-BOC-hydroxystyrene. Other suitable monomers are styrene, a-methylstyrene, or other substituted styrene or vinyl aromatic monomers that, after polymerization, can be chloromethylated to produce a reactive microcarrier intermediate that can be subsequently converted to a functionalized microcarrier. Of course, monomers that do not bear reactive groups (including the crosslinking agent) can be incorporated into the microcarrier. Chemical modification of the reactive microcarrier intermediate may be carried out by a variety of conventional methods.

Figure 4:
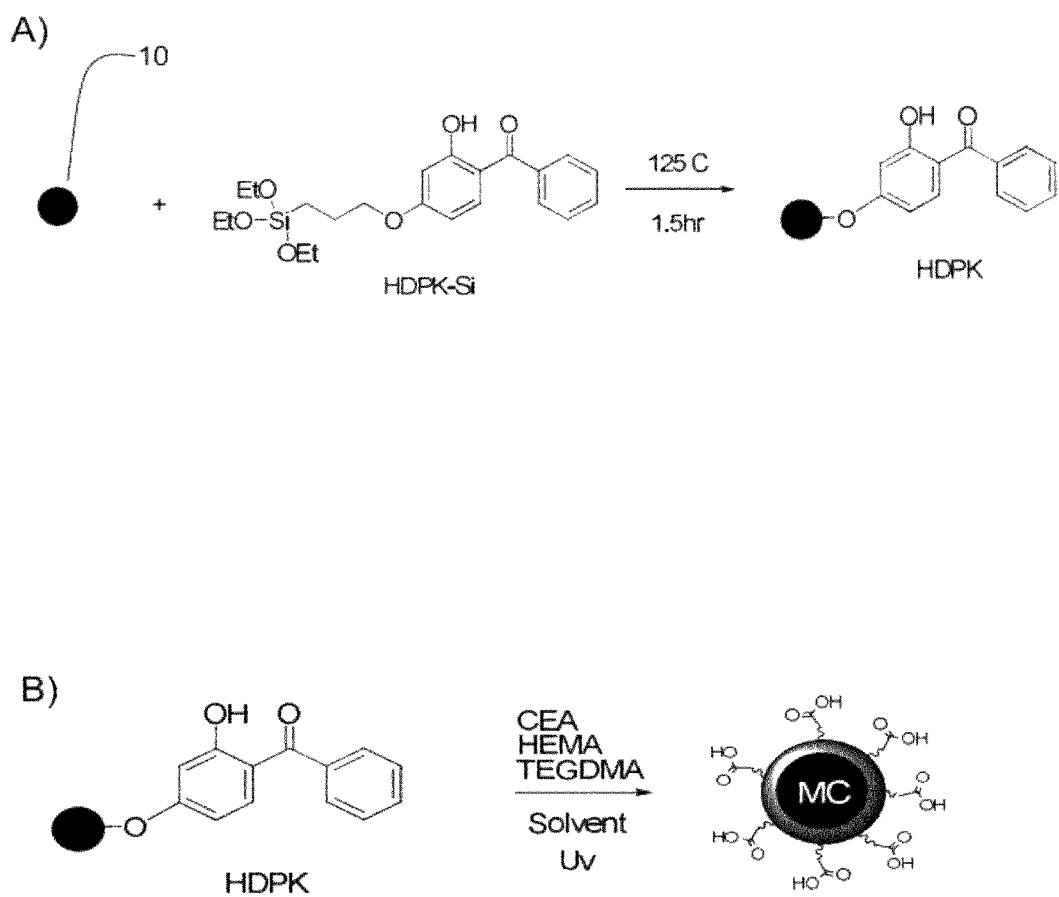
FIGS. 4A-B are collectively a reaction scheme of an embodiment of a method for forming a coated microsphere.

With reference now to FIG. 4, an example of one suitable reaction scheme for immobilizing a polymerization initiator on a microcarrier is shown. In the scheme shown in FIG. 4A, a siloxane modified photoinitiator, HDPK-Si, having silyl ether functionality is conjugated to a glass microcarrier (glass bead) using heat, leaving the bead with hydroxyl diphenylketone (HDPK) conjugated via an ether linkage. Referring now to FIG. 4B, the initiator-conjugated microcarriers are placed in solution with appropriate monomers (in this case 2-carboxyethyl acrylate "CEA", 2-hydroxyethy acrylate "HEMA", tetraethyleneglycol dimethacrylate "TEGDMA") in an appropriate solvent (e.g., methanol) and subjected to UV radiation to initiate polymerization to produce a coated microcarrier. In this case, the microcarrier coating has free carboxylic acid groups resulting from the CEA, which provide for ready conjugation of polypeptides, e.g. as described in more detail below.

With reference now to FIG. 5, an example of one suitable reaction scheme for immobilizing a polymerization initiator on a microcarrier is shown. In the scheme shown in FIG. 5A, a thermal initiator, ABCA, having a carboxylic acid functionality (in this case two carboxylic acid groups) is conjugated to an amine-functionalized microcarrier (amine bead) using 2-ethoxy-1-ethoxycarbonyl-1,2-dihydroquinoline (EEDQ) activation.

Referring now to FIG. 5B, the initiator-conjugated microcarriers are placed in solution with appropriate monomers (in this case 2-carboxyethyl acrylate "CEA", 2-hydroxyethy acrylate "HEMA", tetraethyleneglycol dimethacrylate "TEGDMA") in an appropriate solvent (in this case methanol) and heated to initiate polymerization to produce a coated microcarrier. In this case, the microcarrier coating has free carboxylic acid groups resulting from the CEA, which provide for ready conjugation of polypeptides, e.g. as described in more detail below.

It will be understood that the reaction scheme shown in FIGS. 4-5 is one example of a reaction scheme that may be employed to graft a coating to a microcarrier base, and that any suitable reaction scheme may be employed, depending on the functional groups available on the microcarrier base and the initiator. Further, it will be understood, that while the scheme in FIGS. 4-5 shows the use of a photoinitiator, thermal initiators, RAFT (reversible addition fragment chain transfer) initiator, ATRP (atom transfer radical polymerization) initiators, or other surface initiators may be employed to graft the polymer.

Referring now to FIG. 6, an overview of a method for forming a coated microcarrier is shown. The method includes conjugating a polymerization initiator to a microcarrier base (300) and introducing the initiator-conjugated microcarrier base into a solution containing monomers (310). It will be understood that the "solution" may be a suspension, dispersion, or the like. Polymerization is then initiated to graft the coating to the microcarrier base (320).

By employing the methods outlined in FIGS. 3-6, a coated microcarrier is produced, where the coating is grafted to the microcarrier base via a polymerization initiator. Such grafting of the coating may provide for improved integrity of the coating and reduced delamination during cell culture.

While described with regard to microcarriers, it will be understood that the methods described herein can be used to graft a polymeric coating in situ to a surface of any cell culture article. For example, a polymer layer may be grafted to one or more surfaces of a multi-well plate, a jar, a petri dish, a flask, a multi-layered flask, a beaker, a plate, a roller bottle, a slide, such as a chambered or multi-chambered slide, a tube, a coverslip, a bag, a membrane, a hollow fiber, a cup, a spinner bottle, a perfusion chamber, a bioreactor, or a fermentor. The substrate or base material of such cell culture articles may be formed from any suitable material such as a metallic surface, a ceramic substance, a glass, a plastic, a polymer or co-polymer, any combinations thereof, or a coating of one material on another. For example, the substrate or base material may include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-co-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like. Such material may be readily functionalized as described herein or as known in the art.

5. Polypeptides

Any suitable polypeptide may be conjugated to a coated microcarrier. In various embodiments, polypeptides or proteins are synthesized or obtained through recombinant techniques, making them synthetic, non-animal-derived materials. Preferably, polypeptide includes an amino acid capable of conjugating to the coating; e.g. via the free carboxyl group formed from a monomer used to form the coating. By way of example, any native or biomimetic amino acid having functionality that enables nucleophilic addition; e.g. via amide bond formation, may be included in polypeptide for purposes of conjugating to the coating. Lysine, homolysin, ornithine, diaminoproprionic acid, and diaminobutanoic acid are examples of amino acids having suitable properties for conjugation to a carboxyl group of the microcarrier. In addition, the N-terminal alpha amine of a polypeptide may be used to conjugate to the carboxyl group, if the N-terminal amine is not capped. In various embodiments, the amino acid of polypeptide that conjugates with the coating is at the carboxy terminal position or the amino terminal position of the polypeptide.

In numerous embodiments, the polypeptide, or a portion thereof, has cell adhesive activity; i.e., when the polypeptide is conjugated to the coated microcarrier, the polypeptide allows a cell to adhere to the surface of the peptide-containing coated microcarrier. By way of example, the polypeptide may include an amino sequence, or a cell adhesive portion thereof, recognized by proteins from the integrin family or leading to an interaction with cellular molecules able to sustain cell adhesion. For example, the polypeptide may include an amino acid sequence derived from collagen, keratin, gelatin, fibronectin, vitronectin, laminin, bone sialoprotein (BSP), or the like, or portions thereof. In various embodiments, polypeptide includes an amino acid sequence of ArgGlyAsp (RGD).

Microcarriers as described herein provide a synthetic surface to which any suitable adhesion polypeptide or combinations of polypeptides may be conjugated, providing an alternative to biological substrates or serum that have unknown components. In current cell culture practice, it is known that some cell types require the presence of a biological polypeptide or combination of peptides on the culture surface for the cells to adhere to the surface and be sustainably cultured. For example, HepG2/C3A hepatocyte cells can attach to plastic culture ware in the presence of serum. It is also known that serum can provide polypeptides that can adhere to plastic culture ware to provide a surface to which certain cells can attach. However, biologically-derived substrates and serum contain unknown components. For cells where the particular component or combination of components (peptides) of serum or biologically-derived substrates that cause cell attachment are known, those known polypeptides can be synthesized and applied to a microcarrier as described herein to allow the cells to be cultured on a synthetic surface having no or very few components of unknown origin or composition.

For any of the polypeptides discussed herein, it will be understood that a conservative amino acid may be substituted for a specifically identified or known amino acid. A "conservative amino acid", as used herein, refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

A linker or spacer, such as a repeating poly(ethylene glycol) linker or any other suitable linker, may be used to increase distance from polypeptide to surface of the coated microcarrier. The linker may be of any suitable length. For example, if the linker is a repeating poly(ethylene glycol) linker, the linker may contain between 2 and 10 repeating ethylene glycol units. In some embodiments, the linker is a repeating poly(ethylene glycol) linker having about 4 repeating ethylene glycol units. All, some, or none of the polypeptides may be conjugated to a coated microcarrier via linkers. Other potential linkers that may be employed include polypeptide linkers such as poly(glycine) or poly(β-alanine).

A polypeptide may be conjugated to the coated microcarrier at any density, preferably at a density suitable to support culture of undifferentiated stem cells or other cell types. Polypeptides may be conjugated to a microcarrier at a density of between about 1 pmol per $mm^2$ and about 50 pmol per $mm^2$ of surface of the microcarrier. For example, the polypeptide may be present at a density of greater than 5 $pmol/mm^2$, greater than 6 $pmol/mm^2$, greater than 7 $pmol/mm^2$, greater than 8 $pmol/mm^2$, greater than 9 $pmol/mm^2$, greater than 10 $pmol/mm^2$, greater than 12 $pmol/mm^2$, greater than 15 $pmol/mm^2$, or greater than 20 $pmol/mm^2$ of the surface of the coated microcarrier. In cases where the coating is thick (e.g, <1 um) some polypeptide may be conjugated subsurface making it challenging to estimate polypeptide density by surface area unit. In this case the polypeptide density may be conjugated at a density between 0.1 mmol/mg and about 1 mmol/mg assuming the microcarrier bulk density is between 1.01 and 1.10 cm2/g. Standard BCA colorimetric techniques may be used to estimate peptide density. It will be understood that the amount of polypeptide present can vary depending on the composition of the coating of the microcarrier, the size of the microcarrier and the nature of the polypeptide itself.

A polypeptide may be conjugated to the coated microcarrier via any suitable technique. A polypeptide may be conjugated to a polymerized microcarrier via an amino terminal amino acid, a carboxy terminal amino acid, or an internal amino acid. One suitable technique involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of the swellable (meth)acrylate layer to produce amine reactive NHS esters. EDC reacts with a carboxyl group of the coating layer to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two step procedure. Following activation of the coating, the polypeptide may then be added and the terminal amine of the polypeptide can react with the amine reactive ester to form a stable amide bond, thus conjugating the polypeptide to the coating. When EDC/NHS chemistry is employed to conjugate a polypeptide to the coating, the N-terminal amino acid is preferably an amine containing amino acid such as lysine, ornithine, diaminobutyric acid, or diaminoproprionic acid. Of course, any acceptable nucleophile may be employed, such as hydroxylamines, hydrazines, hydroxyls, and the like.

EDC/NHS chemistry results in a zero length crosslinking of polypeptide to microcarrier. Linkers or spacers, such as polyethylene glycol) linkers (e.g., available from Quanta BioDesign, Ltd.) with a terminal amine may be added to the N-terminal amino acid of polypeptide. When adding a linker to the N-terminal amino acid, the linker is preferably a N-PG-amido-$PEG_X$-acid where PG is a protecting group such as the Fmoc group, the BOC group, the CBZ group or any other group amenable to peptide synthesis and X is 2, 4, 6, 8, 12, 24 or any other discrete PEG which may be available.

In various embodiments, a 1 μM-10 mM polypeptide fluid composition, such as a solution, suspension, or the like, is contacted with an activated coated microcarrier to conjugate the polypeptide. For example the polypeptide concentration may be between about 100 μM and about 2 mM, between about 500 μM and about 1.5 mM, or about 1 mM. It will be understood that the volume of the polypeptide composition and the concentration may be varied to achieve a desired density of polypeptide conjugated to the microcarrier.

The polypeptide may be cyclized or include a cyclic portion. Any suitable method for forming cyclic polypeptide may be employed. For example, an amide linkage may be created by cyclizing the free amino functionality on an appropriate amino-acid side chain and a free carboxyl group of an appropriate amino acid side chain. Also, a di-sulfide linkage may be created between free sulfydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3): 502-6; Koide et al., 1993, Chem. Pharm. Bull. 41(9):1596-1600; or Besse and Moroder, 1997, Journal of Peptide Science, vol. 3, 442-453.

Polypeptides may be synthesized as known in the art (or alternatively produced through molecular biological techniques) or obtained from a commercial vendor, such as American Peptide Company, CEM Corporation, or GenScript Corporation. Linkers may be synthesized as known in the art or obtained from a commercial vendor, such as discrete polyethylene glycol (dPEG) linkers available from Quanta BioDesign, Ltd. Alternatively, polypeptides may be synthesized directly on the surface of the microcarrier support using standard Fmoc/Boc peptide synthesis protocols known in the art.

An example of a polypolypeptide that may be conjugated to a microcarrier is a polypeptide that includes KGGNGEPRGDTYRAY (SEQ ID NO:1), which is an RGD-containing sequence from bone sialoprotein with an additional "KGG" sequence added to the N-terminus. The lysine (K) serves as a suitable nucleophile for chemical conjugation, and the two glycine amino acids (GG) serve as spacers. Cystine (C), or another suitable amino acid, may alternatively be used for chemical conjugation, depending on the conjugation method employed. Of course, a conjugation or spacer sequence (KGG or CGG, for example) may be present or absent. Additional examples of suitable polypeptides for conjugation with microcarriers (with or without conjugation or spacer sequences) are polypeptides that include NGEPRGDTYRAY, (SEQ ID NO:2), GRGDSPK (SEQ ID NO:3) (short fibronectin) AVTGRGDSPASS (SEQ ID NO:4) (long FN), PQVTRGDVFTMP (SEQ ID NO:5) (vitronectin), RNIAEIIKDI (SEQ ID NO:6) (lamininβ1), KYGRKRLQVQLSIRT (SEQ ID NO:7) (mLMα1 res 2719-2730), NGEPRGDTRAY (SEQ ID NO:8) (BSP-Y), NGEPRGDTYRAY (SEQ ID NO:9) (BSP), KYGAASIKVAVSADR (SEQ ID NO:10) (mLMα1 res2122-2132), KYGKAFDITYVRLKF (SEQ ID NO:11) (mLMα1 res 139-150), KYGSETTVKYIFRLHE (SEQ ID NO:12) (mLMα1 res 615-627), KYGTDIRVILNRLNTF (SEQ ID NO:13) (mLMγ1 res 245-257), TSIKIRGTYSER (SEQ ID NO:14) (mLMγ1 res 650-261), TWYKIAFQRNRK (SEQ ID NO:15) (mLMα1 res 2370-2381), SINNNRWHSIYITRFGNMGS (SEQ ID NO:16) (mLMα1 res 2179-2198), KYGLALERKDHSG (SEQ ID NO:17) (tsp1 RES 87-96), or GQKCIVQTTSWSQCSKS (SEQ ID NO:18) (Cyr61 res 224-240).

In some embodiments, the peptide comprises KGGK$^4$DGEPRGDTYRATD$^{17}$ (SEQ ID NO:19), where Lys$^4$ and Asp$^{17}$ together form an amide bond to cyclize a portion of the polypeptide; KGGL$^4$EPRGDTYRD$^{13}$ (SEQ ID NO:20), where Lys$^4$ and Asp$^{13}$ together form an amide bond to cyclize a portion of the polypeptide; KGGC$^4$NGEPRGDTYRATC$^{17}$ (SEQ ID NO:21), where Cys$^4$ and Cys$^{17}$ together form a disulfide bond to cyclize a portion of the polypeptide; KGGC$^4$EPRGDTYRC$^{13}$ (SEQ ID NO:22), where Cys$^4$ and Cys$^{13}$ together form a disulfide bond to cyclize a portion of the polypeptide, or KGGAVTGDGNSPASS (SEQ ID NO:23).

In embodiments, the polypeptide may be acetylated or amidated or both. While these examples are provided, those of skill in the art will recognize that any peptide or polypeptide sequence may be conjugated to a microcarrier as described herein.

6. Incubating Cells in Culture Media Having Microcarriers

Microcarriers as described herein may be used in any suitable cell culture system.

Typically microcarriers and cell culture media are placed in a suitable cell culture article and the microcarriers are stirred or mixed in the media. Suitable cell culture articles include bioreactors, such as the WAVE BIOREACTOR® (Invitrogen), single and multi-well plates, such as 6, 12, 96, 384, and 1536 well plates, jars, petri dishes, flasks, multi-layered flasks, beakers, plates, roller bottles, tubes, bags, membranes, cups, spinner bottles, perfusion chambers, bioreactors, CellSTACK® culture chambers (Corning Incorporated) and fermenters.

A cell culture article housing culture media containing a microcarrier described above may be seeded with cells. The microcarrier employed may be selected based on the type of cell being cultured. The cells may be of any cell type. For example, the cells may be connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoeietic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice or rats, primates including human and non-human primates. In various embodiments, the microcarrier with conjugated polypeptide supports undifferentiated culture of embryonic stem cells for 5 or more passages, 7 or more passages, or 10 or more passages. Typically stems cells are passaged to a new surface after they reach about 75% confluency. The time for cells to reach 75% confluency is dependent on media, seeding density and other factors as know to those in the art.

Because human embryonic stem cells (hESC) have the ability to grown continually in culture in an undifferentiated state, the hESC for use with microcarriers as described herein may be obtained from an established cell line. Examples of human embryonic stem cell lines that have been established include, but are not limited to, BG01V/hOG cells (available from Invitrogen and described herein), H1, H7, H9, H13 or H14 (available from WiCell established by the University of Wisconsin) (Thompson (1998) *Science* 282:1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471): 1636-41, 2005). Embryonic stem cells may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318: 5858).

To maintain stem cells in an undifferentiated state it may be desirable to minimize non-specific interaction or attachment of the cells with the surface of the microcarrier, while obtaining selective attachment to the polypeptide(s) attached to the surface. The ability of stem cells to attach to the surface of a microcarrier without conjugated polypeptide may be tested prior to conjugating polypeptide to determine whether the microcarrier provides for little to no non-specific interaction or attachment of stem cells. Once a suitable microcarrier has been selected, cells may be seeded in culture medium containing the microcarriers.

Prior to seeding cells, the cells, regardless or cell type, may be harvested and suspended in a suitable medium, such as a growth medium in which the cells are to be cultured once seeded. For example, the cells may be suspended in and cultured in a serum-containing medium, a conditioned medium, or a chemically-defined medium. As used herein, "chemically-defined medium" means cell culture media that contains no components of unknown composition. Chemically defined cell culture media may, in various embodiments, contain no proteins, hydrosylates, or peptides of unknown composition. In some embodiments, chemically defined media contains polypeptides or proteins of known composition, such as recombinant growth hormones. Because all components of chemically-defined media have a known chemical structure, variability in culture conditions and thus variability in cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, Xvivo (Lonza), and Stem Cell Technologies, Inc. as mTeSR™1 maintenance media for human embryonic stem cells.

One or more growth or other factors may be added to the medium in which cells are incubated with the microcarriers conjugated to polypeptide. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT) such as activin A, hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-β1 (TGFβ1), and colony stimulating factors.

The cells may be seeded at any suitable concentration. Typically, the cells are seeded at about 10,000 cells/cm$^2$ of microcarrier to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are cultured with the microcarriers may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, (vi) for studying drug and toxicity screening, and (vii) the like.

One suitable way to determine whether cells are undifferentiated is to determine the presence of the OCT4 marker. In various embodiments, the undifferentiated stems cells cultured on microcarriers as described herein for 5, 7, or 10 or more passages retain the ability to be differentiated.

In the following, non-limiting examples are presented, which describe various non-limiting embodiments of the microcarriers and methods discussed above.

EXAMPLES

Example 1

Immobilization of Initiator on Surface of Microcarrier Base

The photoinitiator 2-hydroxy-diphenylketone (HDPK) was covalently bound to the surface of glass beads as follows. Briefly, 1000 mg of dry 200 micrometer low density glass beads (1.04 grams per cubic centimeter) were transferred to a 15 mL centrifuge tube and to it was added 15 mL of 5% (2-hydroxy-4(3-triethoxysilylpropoxy)-diphenylketone) (HDPK-Si) in ethanol and rocked on an orbital shaker for 1 hour. The HDPK solution was removed by aspiration and the beads washed with ethanol (5×10 mL each) aspirating out the majority of residual ethanol on final wash. The beads were then dried in vacuum at 25° C. overnight and the cured in a vacuum oven set at 125° C. for 1.5 hours. (See, e.g., FIG. 4A)

Example 2

Grafting Synthetic Polymer to Initiator-Conjugated Microcarrier Base

A synthetic polymer layer was grafted to the HDPK-conjugated microspheres described in Example 1. Briefly, 100 mg of HDPK glass beads were suspended in 5 mL of water, methanol, or water/methanol (1:1 by volume) and to the solution was added 2-hydroxyethyl acrylate (HEMA, 80 uL), carboxyethyl acrylate (CEA, 20 uL), 10% tetraethyleneglycol dimethacrylate (TEGDMA, 30 uL) in water and in a scintillation vial with a magnetic stirrer (see table below for exact recipes). The reaction was purged under low nitrogen flow for 30 minutes and irradiated for 10 minutes at 350 nm on a Xenon 600w pulsed UV curing system. The coated glass microcarriers were aspiration washed with ethanol, water (3×5 mL each), transferred to a 15 mL centrifuge tube and washed with 10 mL of Ethanol/Water 1:1 overnight on an orbital shaker. Finally, the microcarriers were rinsed with ethanol (3×5 mL each) and air dried overnight. Crystal violet staining confirmed carboxylate grafting, whereas no crystal violet staining was observed in uncured control beads. Cured and uncured beads were prepared described above and as depicted in Tables 1A and 1B below.

TABLE 1A

| | Uncured | | | |
|---|---|---|---|---|
| Experiment | HEMA | CEA | 10% TEGDMA in water | Solvent |
| 15112-114A | 80 uL | 20 uL | 30 uL | water |
| 15112-114B | 80 uL | 20 uL | 30 uL | Water/MeOH 1:1 |
| 15112-114C | 80 uL | 20 uL | 30 uL | MeOH |

TABLE 1B

| | | | Cured | |
| Experiment | HEMA | CEA | 10% TEGDMA in water | Solvent |
|---|---|---|---|---|
| 15112-114D | 80 uL | 20 uL | 30 uL | water |
| 15112-114E | 80 uL | 20 uL | 30 uL | Water/MeOH 1:1 |
| 15112-114F | 80 uL | 20 uL | 30 uL | MeOH |
| 15112-131A x | 80 uL | 20 uL | 30 uL | MeOH (5 mL) |
| 15112-131B 1x | 160 uL | 40 uL | 60 uL | MeOH (5 mL) |
| 15112-131C 3x | 240 uL | 60 uL | 90 uL | MeOH (5 mL) |

Crystal violet staining was performed as follows. Briefly, a small sample of dry COOH functionalized microspheres was placed in a 2 mL centrifuge tube. 500 uL of a 1:5 dilution of crystal violet blue in water was added to the centrifuge tube. After 5 minutes, the sample was aspiration washed with DI water or until top solution was clear and colorless. Staining of the microsphere was assessed using a light microscope. Uniform staining was observed.

The coated microcarriers formed using the water/methanol solvent (see Table 1B, 15512-114E) appeared to be the most uniform (no clumping with slight cloudiness after N2 purge and irradiation) and good crystal violet staining. The coated microcarriers formed in water (see Table 1B, 15512-114D) showed some clumping and cloudiness after N2 purge and irradiation and separation after washing, but showed good crystal violet staining. The coated microcarriers formed in methanol (see Table 1B, 15512-114F) showed no clumping or cloudiness, but a loss of greater than 50% of solvent was observed after N2 purge and irradiation. Like the other microcarriers, the coated microcarriers formed in methanol showed good crystal violet staining.

Figure 7:
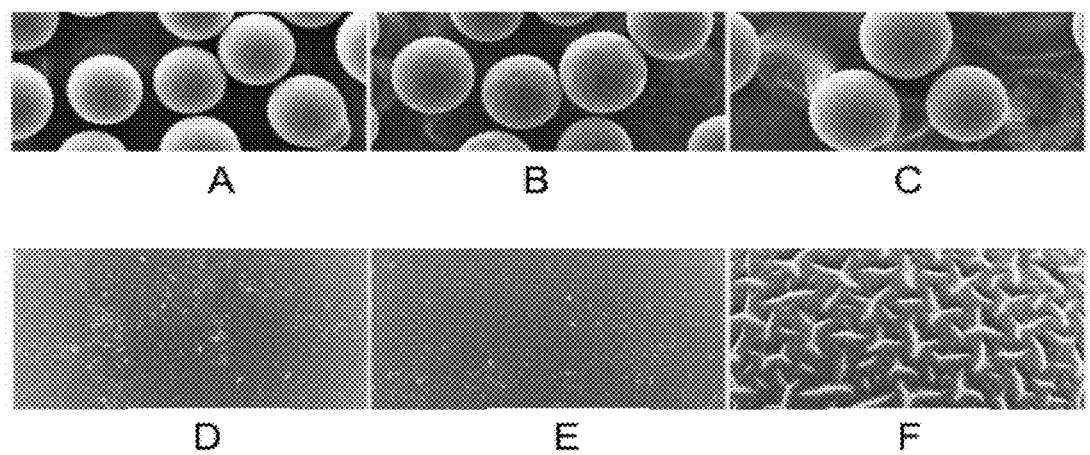
FIG. 7A-F shows scanning electron micrographs of A) PS—NH$_2$ as received from vendor (FIGS. 7A and 7D), B) ABCA covalently attached to PS (FIGS. 7B and 7E), and C) HG02 grafted onto PS-ABCA (FIGS. 7C and 7F).

The resulting microcarriers were observed via scanning electron microscope (see, FIG. 7). The amine functionalized polystyrene (PS—NH$_2$, FIGS. 7A and 7D) and ABCA-derivatized PS (PS-ABCA, FIGS. 7B and 7E) had more or less the same surface texture (observed at both 100× and 1000× magnification). We did see slight deformation at the surface of the PS-ABCA presumably due to the solvent induced swelling and collapsing during attachment of ABCA. When the PS-ABCA surface was grafted with HG02 (FIGS. 7C and 7F), a random pattern of divots were observed at the surface. "HG02" refers to a swellable (meth)acrylate coating formed from polymerization of HEMA, CEA and TEGDMA having a volume ratio of 80:20:3, respectively (see, e.g., Table 1B). These divots were not obvious under the light microscope where the beads were suspended in aqueous solution and polymer swelling occurred. SEM images were captured on dry beads and the divots may be due to the collapsing of the polymer.

Example 3

Grafting of Polypeptide to Coated Microcarrier

A polypeptide was grafted to the coated microcarrier described in Example 2. Briefly, 50 mg of dry low density glass (Idg)-HDPK-HG02 beads (15112-114 D,E,F) was transferred to a 2 mL centrifuge tube. 1 mL of EDC/NHS (200/50 mM) in water solution was added to the beads and mixed on an orbital shaker for 60 min. The solution was spun down, aspirated, rinsed once with water spin/aspirated. 1 mL of 1 to 10 mM Vitronectin (Ac-KGGPQVTRGDVFTMP-NH2, SEQ ID NO:26) spiked with 0.25% of a Rhodamine labeled peptide sequence (TAMRA-Gly-Arg-Gly-Asp-Ser-Pro-Ile-Ile-Lys-NH$_2$ (SEQ ID NO:25) (see below) was added and allowed to mix for 60 min. The peptide solution was removed by spin/aspiration and the beads were treated with 1.5 mL of 1M ethanolamine pH 8 for 30 min followed by washing with PBS (1.5 mL×5), 1% SDS (1×1.5 mL×15 min), and DI water and ethanol (1.5 mL×5) and air dried overnight.

Example 4

Rhodamine Florescence to Verify Polypeptide Conjugation to Coating

Figure 8:
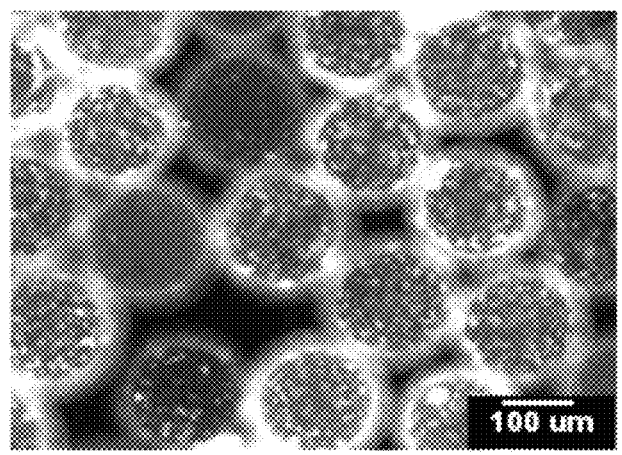
FIG. 8 is a fluorescence image of rhodamine labeled vitronectin-conjugated coated microspheres.

Rhodamine excited fluorescence was observed in coated microspheres with conjugated polypeptide (EXAMPLE 3). Briefly, fluorescence was assessed on a Ziess Axiovert 200M inverted microscope equipped with the HB 100 Fluorescent lamp attachment. Rhodamine excitation with exposure time between 5 to 100 miliseconds was used to excite tetramethylrhodamine fluorophore. Brightfield and fluorescent images were processed with AxioVision 4.62 software. A resulting florescent image is shown in FIG. 8. Uniform fluorescence was observed, suggesting that the polypeptide successfully conjugated to the coating. The control surface (Vitronectin polypeptide with no EDC/NHS activation) gave very low florescence when analyzed under the same exposure.

Example 5

Peptide Density Estimation

Figure 9A:
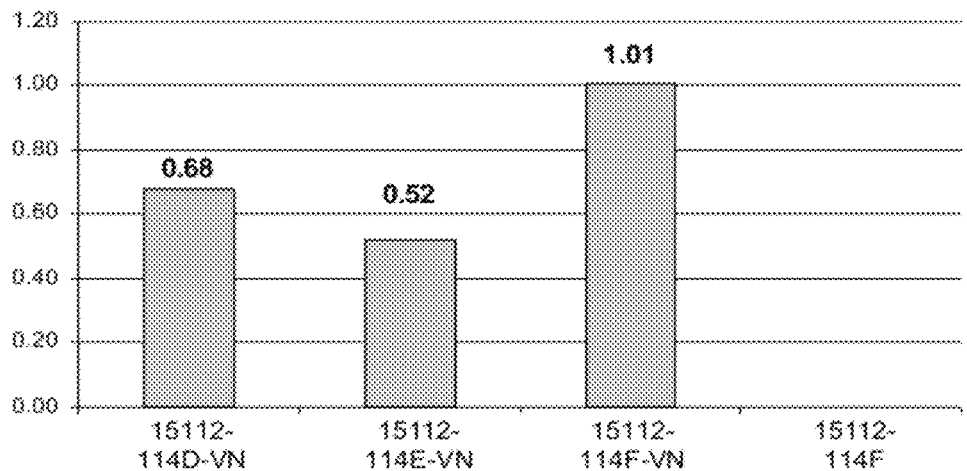
FIG. 9A is a bar graph showing estimated polypeptide density of vitronectin (VN)-conjugated coated microspheres where the coating was formed in situ using different solvents (water, water/methanol, and methanol).

The density of polypeptide conjugated to the coated microcarrier was estimated by and Interchem (211 Bis, Avenue Kennedy, BP 1140, 03103 Montiucon Codex, France) bicinchoninic acid (BCA) assay. Briefly, the BCA working reagent was prepared by adding 1 part of reagent B to 50 parts of reagent A in a 50 mL centrifuge tube. The standard solutions were prepared by serial dilution of a 10 mM Vitronectin solution down to 1 uM. 10 mg of dry VN modified microcarriers were added to separate wells of a Corning ultra low attachment (ULA) 24 well plate. 25 µl of each standard solution was also introduced into separate wells of the ULA 24 well plate. To each standard solution and sample was added 8000 of the BCA working reagent per test well and the plate was incubated for 2 hours at 25° C. (gently mixing the plate every 30 min to re-suspend microcarriers). 750 uL of BCA color developed standard and sample solutions were removed (place pipette tip in corner of well to minimize transfer of beads from sample well) and the optical absorbance was read at 562 nm (instrument blanked with PBS). To estimate peptide density, the blank absorbance was subtracted from all others to get net absorbance to generate a standard curve of net absorbance as a function of VN concentration. The linear fit up to 5 mM was used to generate a correlation formula. The absorbance of the base bead (15112-114F, no VN) was subtracted from VN-sample absorbance to get the sample net absorbance. The correlation formula was then used to estimate peptide density in nmol/mg and pmol/mm$^2$. The results are shown in FIG. 9A.

Figure 9B:
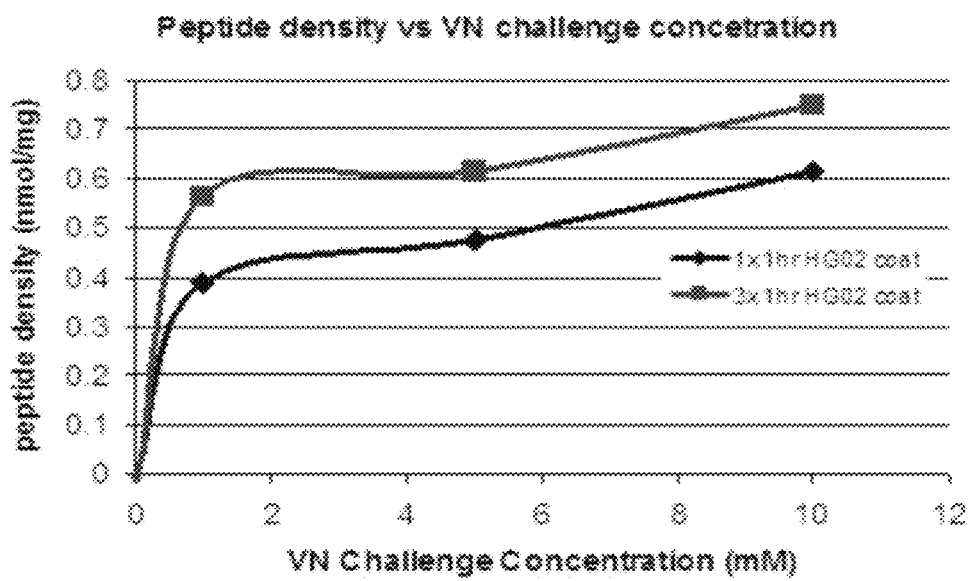
FIG. 9B is a graph showing estimated peptide density on 1×1 hr and 3×1 hr PS-ABCA-HG02 grafted beads after being conjugated with increasing amounts of VN peptide.

BCA analysis was also employed to estimate the peptide density on "3×1 hr HG02 coating (15112-131C 3×) and the "1×1 hr" coating (15112-131B 1×) at all VN challenge concentrations. BCA analysis revealed a slightly higher peptide density on the "3×1 hr" HG02 coating compared to the "1×1 hr" coating, which may be related to differences in coating thickness as some of the peptide is believed to be subsurface (see FIG. 9B). Overall, both surfaces showed a clear relationship between peptide density and VN challenge concentration (in the range of 0.4 and 0.8 nmol/mg of bead for 1 to 10 mM VN challenges). The conjugation efficiency was ~3% for the 1 mM conjugation and decreased as the VN challenge concentration increased. A fluorescent shell surrounding the polystyrene core was observed by confocal microscopy, and of further confirmed the HG02 coating and peptide conjugation.

Example 6

Cell Adhesion Assay

Figure 10:
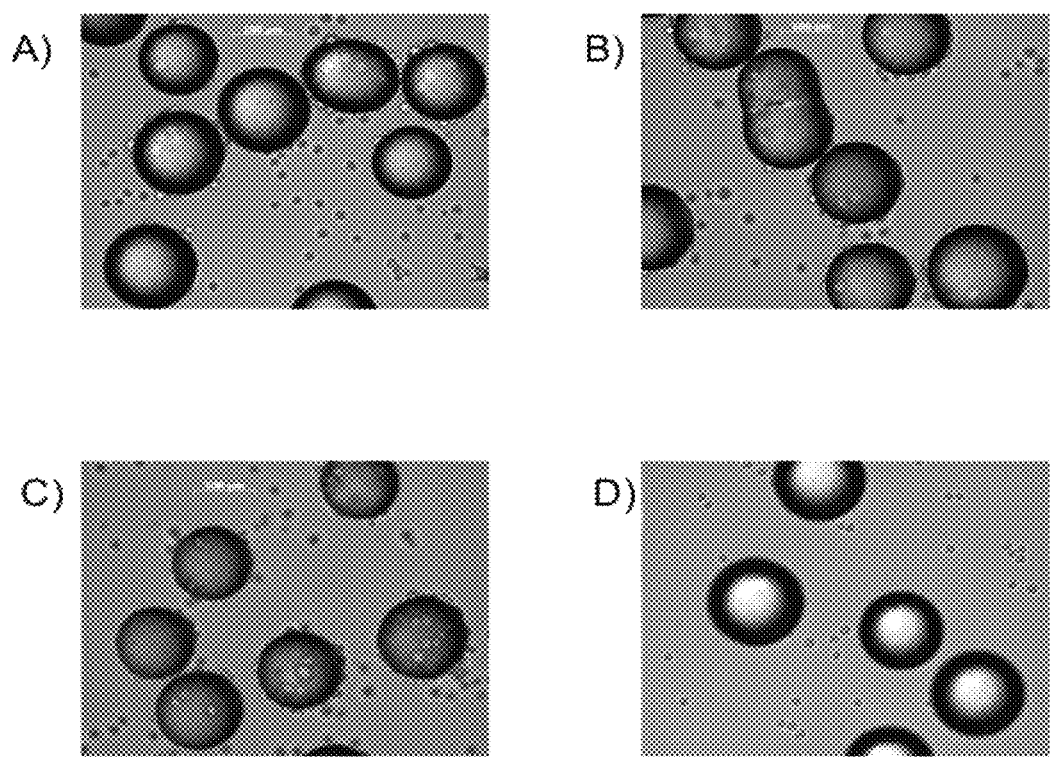
FIGS. 10A-D are brightfield images of HT1080 cell adhesion to vitronectin (VN)-conjugated coated microspheres where the coating was formed in situ using different solvents; specifically water (A), water/methanol (B), and methanol (C), and to coated microspheres without coated vitronectin (D).

HT1080 cells were trypsinized and allowed to recover in Iscove's Modified Dulbecco's Medium (IMDM) with 10% Fetal Bovine Serum (FBS) for 30 minutes at 37° C., 5% $CO_2$. After recovery, the cells were washed and resuspended in 0.1% Bovine Serum Albumin (BSA) in Iscove's Modified Dulbecco's Media (IMDM). Approximately 3 mg of vitronectin-derivatized microcarriers was transferred to a 2 mL centrifuge tube and blocked with 2 mL of 1% BSA in D-phosphate buffered saline (D-PBS) for 1 hr at room temperature. The microspheres were then washed with 2 mL of D-PBS, resuspended in 200 ul of 0.1% BSA in IMDM prior to cell seeding and placed in 24 well Corning Ultra low attachment microplate. 200 uL of resuspended cells were placed in each well of the 24 well Corning Ultra low attachment microplate. Bead/cell suspension was incubated for 1 hr at 37 C, 5% $CO_2$. The media was removed and the beads were washed in the wells with D-PBS (2×2 mL). Cellular attachment and spreading was assessed using Ziess Axiovert 200M inverted microscope. Images of the cells adhered to the microcarriers are shown in FIG. 10.

FIG. 10A is an image of cells cultured with \TN-conjugated coated glass microspheres in which the coating was formed in water. FIG. 10B is an image of cells cultured with VN-conjugated coated glass microspheres in which the coating was formed in a water/methanol solvent. FIG. 10C is an image of cells cultured with VN-conjugated coated glass microspheres in which the coating was formed in methanol. FIG. 10D is an image of cells cultured with coated glass microspheres in which the coating was formed in methanol and no VN was conjugated to the coating. Each of the VN-conjugated coated microspheres supported adhesion of HT1080 cells (FIGS. 10A-C). In contrast, no cell attachment was observed to the microcarriers with no VN polypeptide (FIG. 10D).

Example 7

Immobilization of Initiator on Surface of Microcarrier Base

The thermal initiator 4,4'-azobis(4-cyanovaleric acid) (ACBA) was covalently bound to the surface of an amine bead as follows. Briefly, ACBA (112 mg, 280 g/mol, 0.4 mmol) and 2-ethoxy-1-ethoxycarbonyl-1,2,-dihydroxyquinoline (EEDQ) (197 mg, 247 g/mol, 0.8 mmol) were dissolved in 5 mL of N,N-dimethylformamide (DMF), added to a peptide synthesis vessel and bubbled with nitrogen gas for 10 min. 1 g of dry amine-functionalized polystyrene microspheres (Polystyrene AM-$NH_2$, Rapp Polymere GMBH, particle size 250-315 um, 1.09 mmol NH2/g), having

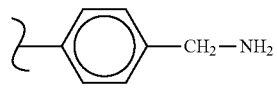

as a functional group, was added to the vessel. The amine-functionalized beads were mixed by nitrogen bubbling for 24 hours. The microspheres were filtered washed with DMF and ethanol (5×10 mL each) and dried overnight under vacuum.

Example 8

Grafting Synthetic Polymer to Initiator-Conjugated Microcarrier Base

A synthetic polymer layer was grafted to the ABCA-conjugated microspheres described in Example 1. Briefly, 100 mg of ABCA-immobilized microspheres was combined with 2-hydroxyethy acrylate (HEMA, 160 µL), 2-carboxyethyl acrylate (CEA, 40 µL), tetraethyleneglycol dimethacrylate (TEGDMA, 6 µL) in 5 mL of methanol in a glass scintillation vial equipped with a magnetic stirrer. The suspension was degassed with nitrogen for 1 hr at room temperature, and then at 80° C. for 30 minutes to 3 hours. The polymer grafted microspheres were aspiration washed with methanol and DMF (2×10 mL), transferred to a 15 mL centrifuge tube washed with 10 mL of Ethanol/Water 1:1 on an orbital shaker overnight. The beads were then washed with ethanol (3×5 mL each) and dry under vacuum overnight.

Example 9

Grafting of Polypeptide to Coated Microcarrier

A polypeptide was grafted to the coated microcarrier described in Example 2.

Briefly, 50 mg of dry, coated microspheres (~300 um particle size) was transferred to a 2 mL centrifuge tube. 94 mg of 1-ethyl-3-[3-dimethylaminopropyl]carbodiimide hydrochloride (EDC) (12 equiv, 191.70 g/mol, 492 umol) and 14 mg N-hydroxysuccinimide (NHS) (3 equiv, 115 g/mol, 123 umol) was dissolved in 1.5 mL of DMF and added to the beads and allowed to mix on an orbital shaker for 60 min. The solution was aspirated, rinsed once with DMF, aspirated and then 1 mL of Vitronectin (Ac-KGGPQVTRGDVFTMP-NH2, SEQ ID NO:26) or Vitronectin RGD scrambled (Ac-KGGPQVTGRDVFTMP-NH2, SEQ ID NO:24) [1 to 10 mM in borate buffer, pH 9.2, spiked with 0.25% Rhodamine peptide spiked (5/6TAMRA-Gly-Arg-Gly-Asp-Ser-Pro-Ile-Ile-Lys-$NH_2$ (SEQ ID NO:25) was added and allowed mix for 60 min. The peptide solution was removed by aspiration and the beads were treated with 1.5 mL of 1M ethanolamine pH 8 for 10 min followed by washing with PBS (1.5 mL×5), 1% SDS (1×1.5 mL×1.5 min), and DI Water and ethanol (1.5 mL×5) and dried under a gentle stream of nitrogen.

Example 10

FTIR Verification of ABCA Conjugation and Thermal Grafting of Coating Layer

Figure 11:
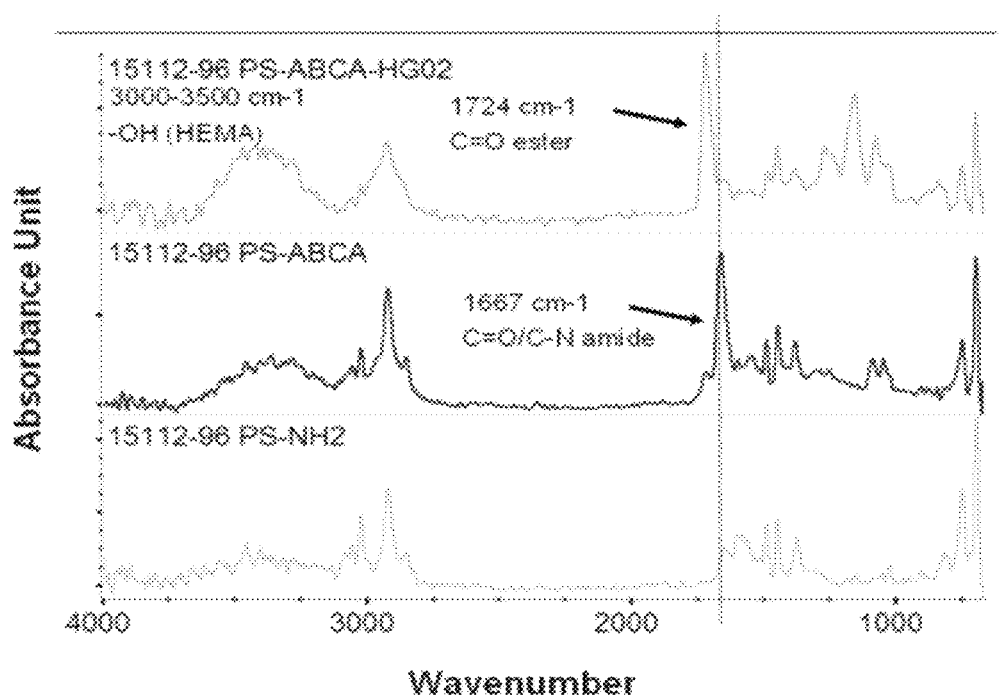
FIG. 11 is a graph of absorbance units over wavenumber of on-bead FTIR analysis of a microbead base (bottom panel), an initiator-conjugated bead (middle panel), and a microbead with a coating grafted to the bead (top panel).

Fourier transform infrared (FTIR) spectroscopy was used to verify that the ABCA was successfully immobilized on the beads and to verify that the coating was grafted to the beads. Briefly, bead samples were analyzed on a Thermo Electron Corporation (Waltham, Mass.) Nicolet Avatar using the OmniSampler ATR attachment (single bounce germanium crystal) with the instrument set at 50 scans and a resolution of 4. Small samples of beads were gently pressed on the on the surface of the germanium crystal using a screw press prior to analysis. As shown in FIG. 11, a peak at 1 1667 cm$^{-1}$ corresponding to C=O amide was seen in the ABCA-conjugated beads (middle panel), suggesting that ABCA covalently attached to the bead via the nitrogen of the amine. Beads coated as described in Example 8 produced a peak at 3000-3700 cm$^{-1}$ corresponding to a hydroxyl group, which would be expected to be present in the polymer as a result of the HEMA monomer. Further, a peak at 1724 cm$^{-1}$ corresponding to an expected C=O ester in the resulting coating (from the acrylate monomers) was observed (FIG. 11, top panel), suggesting that the coating grafted to the microsphere.

Example 11

Crystal Violet Staining to Verify Coating of Microbeads

Figure 12:
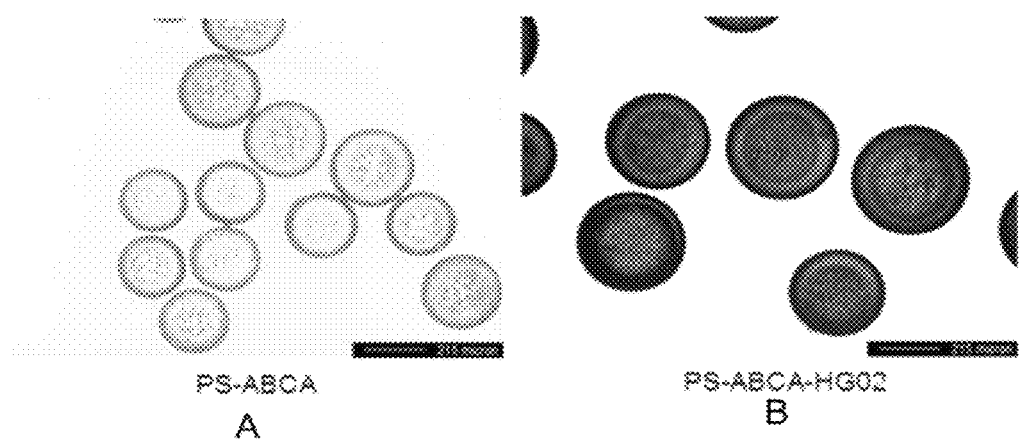
FIGS. 12A and B shows images of crystal violet stained initiator conjugated microbeads (FIG. 12A) and crystal violet stained microbeads with a coating grafted to the beads (FIG. 12B).

Crystal violet staining of ABCA-conjugated microbeads (EXAMPLE 7) and polymer coated microbeads (EXAMPLE 8) was performed to verify that the polymer layer was grafted to the beads. Briefly, small samples of the dry microbeads were placed in a 2 mL centrifuge tube. 500 uL of a 1:5 dilution of crystal violet blue in water was added to the centrifuge tube. After 5 minutes, the sample was aspiration washed with DI water or until top solution was clear and colorless. Staining of the microspheres was assed using a light microscope and representative images are presented in FIG. 12. FIG. 12 shows images of crystal violet stained initiator conjugated microbeads (FIG. 12A) and crystal violet stained microbeads with a coating grafted to the beads (FIG. 12B). As shown in FIG. 12, the coated microspheres were uniformly stained, while the uncoated microspheres were un-stained, suggesting that the in situ polymerization coating process successfully resulted in coated microspheres.

Example 12

Rhodamine Florescence to Verify Polypeptide Conjugation to Coating

Figure 13:
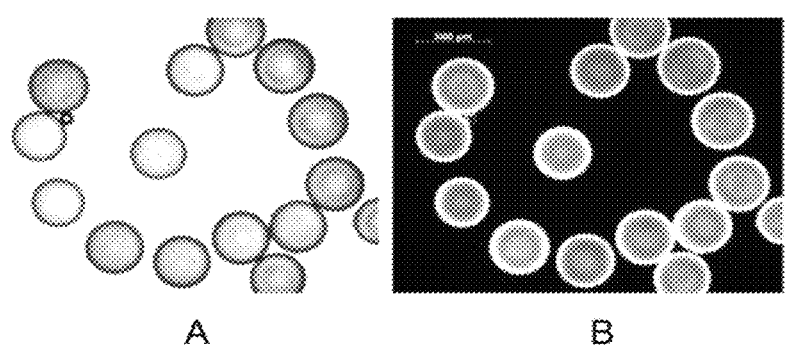
FIG. 13 shows brightfield (FIG. 13A) and fluorescence (FIG. 13B) images of a rhodamine-conjugated polypeptide conjugated to coated microspheres.

Rhodamine excited fluorescence was observed in coated microspheres with conjugated polypeptide (EXAMPLE 9). Briefly, fluorescence was assessed on a Ziess Axiovert 200M inverted microscope equipped with the HB 100 Fluorescent lamp attachment. Rhodamine excitation with exposure time between 5 to 100 miliseconds was used to excite tetramethylrhodamine fluorophore. Brightfield and fluorescent images were processed with AxioVision 4.62 software. Resulting brightfield and florescent images are in FIG. 13. Uniform fluorescence was observed, suggesting that the polypeptide successfully conjugated to the coating. The control surface (vitronectin polypeptide with no EDC/NHS activation) gave very low florescence when analyzed under the same exposure.

Example 13

Cell Adhesion Assay

Figure 14:
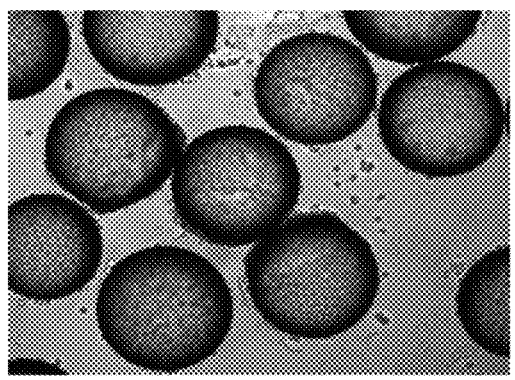
FIG. 14 shows brightfield images of HT1080 cell adhesion on vitronectin peptide (FIG. 14A) and vitronectin RGD scrambled peptide (FIG. 14B) conjugated to coated microbeads.
Figure 14:
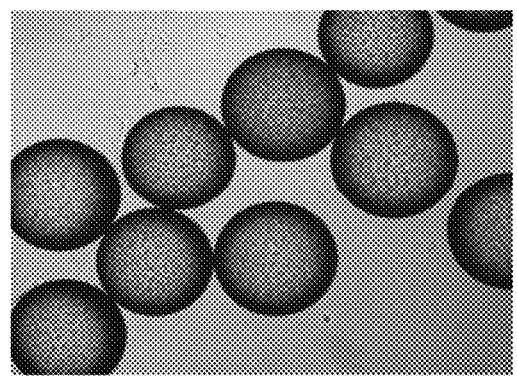

Cells were trypsinized and allowed to recover in Iscove's Modified Dulbecco's Medium (IMDM) with 10% Fetal Bovine Serum (PBS) for 30 minutes at 37° C., 5% $CO_2$. After recovery, the cells were washed and resuspended in 0.1% Bovine Serum Albumin (BSA) in IMDM. Approximately 3 mg of vitronectin-derivatized microcarriers (Ac-KGG-PQVTRGDVFTMP-NH2, SEQ ID NO:26) was transferred to a 2 mL centrifuge tube and blocked with 2 mL of 1% BSA in D-PBS for 1 hr at room temperature. The microspheres were then washed with 2 mL of D-PBS, resuspended in 200 ul of 0.1% BSA in IMDM prior to cell seeding and placed in 24 well Corning Ultra low attachment microplate. 200 uL of resuspended cells were placed in each wells of the 24 well Corning Ultra low attachment microplate. Bead/cell suspension was incubated for 1 hr at 37 C, 5% $CO_2$. The media was removed and the beads were washed in the wells with D-PBS (2×2 mL). Cellular attachment and spreading was assessed using Ziess Axiovert 200M inverted microscope. Images of the cells adhered to the microcarrier are shown in FIG. 14A. When the microcarrier was conjugated with the vitronectin RGD scrambled sequence (Ac-KGGPQVTGRDVFTMP-NH2, SEQ ID NO:24), no cells adhered to the microcarriers also shown in FIG. 14B.

Example 14

Human Embryonic Stem Cell (hESC) Adhesion and Expansion

As a standard, polystyrene beads (Sigma) were coated over night at 4 C under constant agitation with GFR-Matrigel. Prior to the assay the beads were decanted, and Matrigel in solution was removed. The beads were then resuspended in mTERS1 medium.

BG01V/hOG human embryonic stem cells (Invitrogen) were maintained on Matrigel coated TCT 75 Flask (Corning) in serum free mTERS1 medium containing 50 ug/ml Hygromycin B (STEMCELL Technologie). Daily medium changes began after the first 48 h in culture. Cells were passaged every 5 to 6 days using collagenase IV (Invitrogen) and mechanical scraping. For the assay, aggregate colonies were harvested and resuspended in fresh mTERS1 medium. Cells were seeded to the 24 wells Corning Ultra low attachment microplate (1.5×10$^5$ cells per cm2) containing the microcarriers of the present invention or Cytodex™ 3 microcarrier available from GE Healthcare as a comparative example. The volume was adjusted to 600 microliters with culture medium. Cells were allowed to attach to the microcarriers for 48 h without agitation. 2 days after seeding, cellular attachment and spreading was assessed using Ziess Axiovert 200M inverted microscope. Quantitative analysis was also performed as followed. The media was removed and the beads were washed in the wells with D-PBS (2×3 mL). The D-PBS was removed and replaced with 200 microliters of CellTiter-Glo reagent (Promega). Microplate was placed in the shaker for 10 min at RT and Luminescence was measured. For the cell expansion assay, same seeding protocol was used and cells were maintained in static condition over the course of cell expansion. After 48 h cell attachment, culture medium was changed daily after sedimentation of the cells and the beads. After 5 days, cell spreading and cell quantification were assessed using the same methods describe above.

Figure 15:
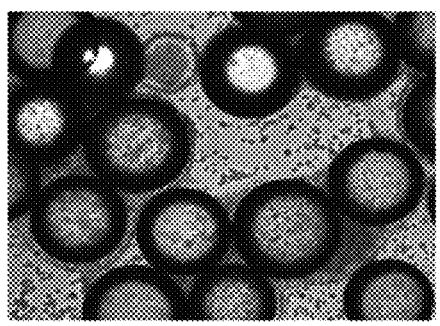
FIG. 15 is a microscopy image illustrating BG01V/hOG cells growth on Vitronectin peptide grafted PS-ABCA-HG02 microcarriers 5 days after seeding, with FIG. 15A being a brightfield image, and FIG. 15B being a fluorescence, FITC, image.
Figure 15:
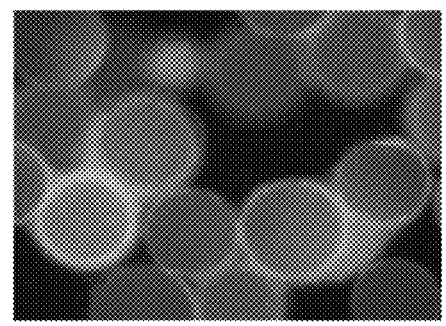
Figure 16:
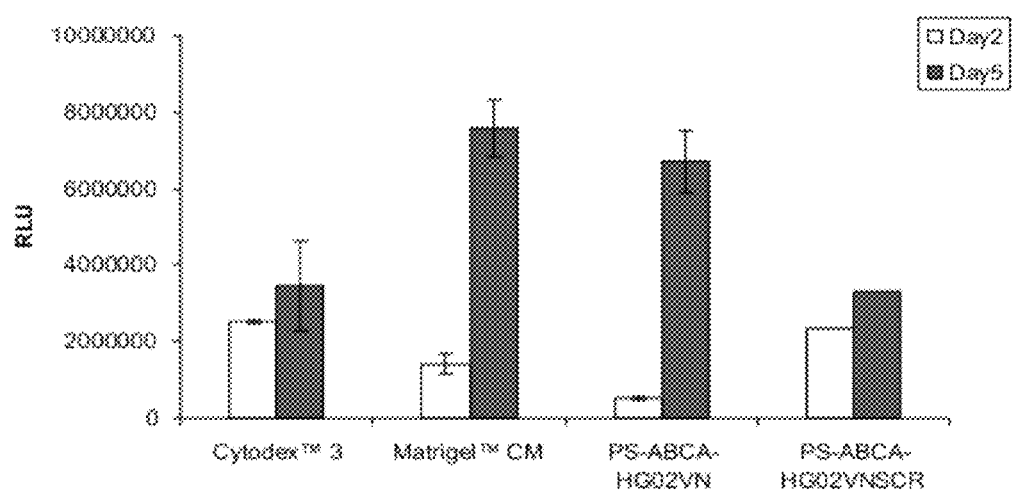
FIG. 16 is a graph showing quantification of BG01V/hOG cells after 2 days and 5 days culture performed on peptide grafted PS-ABCA-HG02 microcarriers (PS-ABCA-VN or PS-ABCA-VN-SCR), on Matrigel coated beads (Matrigel™CM) and Cytodex™ 3 as comparative example.

FIG. 15 is a microscopy image illustrating BG01V/hOG cells growth on Vitronectin peptide grafted PS-ABCA-HG02 microcarriers 5 days after seeding. FIG. 15A is a brightfield image, and FIG. 15B is a fluorescence, FITC, image. As shown in the FIG. 15B, hESC were Oct4 positive, and therefore maintained their pluripotent state. FIG. 16 is a graph showing quantification of BG01V/hOG cells after 2 days and 5 days culture performed on peptide grafted PS-ABCA-HG02 microcarriers (noticed PS-ABCA-VN or PS-ABCA- VN-SCR), on Matrigel coated beads (Matrigel™CM) and Cytodex™ 3 as comparative example. The graph clearly shows the advantage provided by the VN-swellable (meth) acrylate microcarriers after 5 days culture over collagen coated microcarriers from the prior art. Furthermore, this graph shows also that the VN-swellable (meth)acrylate microcarrier performed as well as the Matrigel coated beads described in the prior art, which have previously been considered to be the gold standard for culture of human embryonic stem cells.

Thus, embodiments of SYNTHETIC MICROCARRIERS FOR CULTURING CELLS are disclosed. One skilled in the art will appreciate that the microcarriers and methods described herein can be practiced with embodiments other than those disclosed. The disclosed embodiments are presented for purposes of illustration and not limitation.

What is claimed is:

1. An article for cell culture, comprising:
   a base; and
   a polymeric coating grafted to the base via a polymerization initiator or a remnant thereof
   the polymeric coating comprising a swellable (meth)acrylate polymer having an equilibrium water content of between 5% and 70%
   wherein the polymeric coating is formed from a mixture of monomers comprising a carboxyl group-containing (meth)acrylate monomer, a cross-linking (meth)acrylate monomer, and a hydrophilic monomer capable of polymerizing with the carboxyl group-containing (meth) acrylate monomer and the cross-linking (meth)acrylate monomer,
   wherein the weight percentage of the polymer derived from the hydrophilic monomer is between 60% and 90%, the weight percentage of the polymer derived from the carboxyl group-containing monomer is between 10% and 40%, and the weight percentage of the polymer derived from the cross-linking monomer is between 1% and 10%; and,
   a cell adhesive polypeptide having an RGD sequence to the polymer.

2. The article according to claim 1, wherein the article is a microcarrier.

3. The article according to claim 1, wherein the base comprises glass or polystyrene.

4. The article according to claim 1, wherein the polymerization initiator or remnant thereof is conjugated to the base via an amide bond.

5. The article of claim 1 wherein a surface of the base comprises a silanol group and the polymerization initiator comprises a hydrolysable group.

6. The article of claim 1 wherein a surface of the base comprises a silanol group and the polymerization initiator comprises a silyl ether.

7. The article of claim 6, wherein the polymerization initiator has the formula:

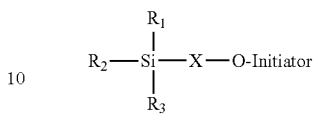

where
   $R_1$, $R_2$, and $R_3$ are each independently C1-C3 alkyl, alkoxy, or hydrogen; and
   X is C1-C6 straight or branched chain alkyl and is present or absent.

8. The article of claim 6, wherein the polymerization initiator is an alkoxy-substituted silyl benzophenone.

9. The article of claim 8, wherein the polymerization initiator is 2-hydroxy-4(3-triethoxysilylpropoxy)diphenylketone.

10. The article of claim 1, wherein the surface of the article comprises an amine group, a carboxyl group or an hydroxyl group,
    wherein if the article comprises an amine group, the polymerization initiator comprises a carboxyl group,
    wherein if the article comprises a carboxyl group, the polymerization initiator comprises an amine group or an hydroxyl group, and
    wherein the polymerization initiator is conjugated to the surface of the article via formation of an amide bond or an ester bond.

11. The article of claim 10 wherein the polymerization initiator comprising a carboxyl or hydroxyl group is selected from the group consisting of 4,4'-azobis(4-cyanovaleric acid); 4-benzoyl benzoic acid; 2,2'-azobis[2-methyl-N-(2-hydroxyethyl)propionamide]; and 2,2'-azobis{2-methyl-N-[1,1-bis(hydroxymethyl)-2-hydroxyethyl]propionamide}.

12. The article of claim 1, wherein the carboxyl group-containing (meth)acrylate monomer comprises free carboxyl groups after the monomer is incorporated into the polymer.

13. The article of claim 2, wherein the microcarrier comprises a glass bead or a polystyrene bead.

14. A method for culturing cells on the article of claim 2, comprising: contacting cells with a cell culture medium containing said microcarriers of claim 2 and culturing the cells in the medium.

* * * * *